(12) United States Patent
Hladio et al.

(10) Patent No.: US 11,666,407 B2
(45) Date of Patent: Jun. 6, 2023

(54) SYSTEMS AND METHODS FOR SURGICAL NAVIGATION, INCLUDING IMAGE-GUIDED NAVIGATION OF A PATIENT'S HEAD

(71) Applicants: INTELLIJOINT SURGICAL INC., Waterloo (CA); Andre Novomir Hladio, Waterloo (CA); Richard Tyler Fanson, Stoney Creek (CA); Eric J. Ryterski, Louisville, CO (US); Rowan Ferrabee, Waterloo (CA); Rafa Narciso, Waterloo (CA)

(72) Inventors: Andre Novomir Hladio, Waterloo (CA); Richard Tyler Fanson, Stoney Creek (CA); Eric J. Ryterski, Louisville, CO (US); Rowan Ferrabee, Waterloo (CA); Rafa Narciso, Waterloo (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 1098 days.

(21) Appl. No.: 16/331,236

(22) PCT Filed: Sep. 7, 2017

(86) PCT No.: PCT/IB2017/055400
§ 371 (c)(1),
(2) Date: Mar. 7, 2019

(87) PCT Pub. No.: WO2018/047096
PCT Pub. Date: Mar. 15, 2018

(65) Prior Publication Data
US 2019/0183590 A1    Jun. 20, 2019

Related U.S. Application Data

(60) Provisional application No. 62/384,410, filed on Sep. 7, 2016.

(51) Int. Cl.
*A61B 46/00* (2016.01)
*A61B 46/10* (2016.01)
(Continued)

(52) U.S. Cl.
CPC .............. *A61B 46/00* (2016.02); *A61B 34/10* (2016.02); *A61B 46/10* (2016.02); *A61B 90/14* (2016.02);
(Continued)

(58) Field of Classification Search
None
See application file for complete search history.

(56) References Cited

U.S. PATENT DOCUMENTS

| 5,662,111 A | 9/1997 | Cosman |
| 6,529,765 B1 | 3/2003 | Franck et al. |
| 2007/0021738 A1 | 1/2007 | Hasser et al. |
| 2012/0078236 A1 | 3/2012 | Schoepp |

(Continued)

FOREIGN PATENT DOCUMENTS

| JP | 2012-050887 A | 3/2012 |
| WO | 2011134083 A1 | 11/2011 |
| WO | 2016058076 A1 | 4/2016 |

OTHER PUBLICATIONS

Notice of Reasons for Refusal for Corresponding Japanese Patent Application No. P2019-513888 dated Aug. 10, 2021; 4 Pages and With English Translation.
(Continued)

*Primary Examiner* — Jonathan Cwern

(57) ABSTRACT

Systems, methods and devices are described herein for performing a navigated surgical procedure involving a patient's anatomy in sterile and non-sterile surgical environments. A camera may be used to determine a registration of the camera coordinate-frame to the patient anatomy or optionally a tracker in relation to the patient anatomy. A (Continued)

drape may be applied to permit use in a sterile surgical environment. The camera may be moved from its original position to enable access to patient anatomy while maintaining a registration of the camera coordinate-frame with the patient anatomy. Alternatively, the camera may be used in a hand-held or head-mounted manner. A visualization of the patient anatomy may be displayed on a computing unit, with visualization reference planes defined by the pose of an instrument or the camera. The visualization may be presented on a display of a computing unit or as part of a head mounted augmented reality system.

20 Claims, 17 Drawing Sheets

(51) Int. Cl.
*A61B 90/57* (2016.01)
*A61B 90/14* (2016.01)
*A61B 34/10* (2016.01)
*A61B 90/50* (2016.01)
*A61B 50/13* (2016.01)
*A61B 34/20* (2016.01)
*A61B 90/00* (2016.01)

(52) U.S. Cl.
CPC .............. *A61B 90/50* (2016.02); *A61B 90/57* (2016.02); *A61B 50/13* (2016.02); *A61B 2034/2055* (2016.02); *A61B 2034/2057* (2016.02); *A61B 2034/2072* (2016.02); *A61B 2090/3983* (2016.02); *A61B 2090/3991* (2016.02)

(56) References Cited

U.S. PATENT DOCUMENTS

| | | | |
|---|---|---|---|
| 2012/0157887 A1* | 6/2012 | Fanson | A61F 2/46 600/595 |
| 2013/0327836 A1 | 12/2013 | Prpa | |
| 2014/0261456 A1 | 9/2014 | Malackowski et al. | |
| 2014/0275940 A1* | 9/2014 | Hladio | A61B 5/1072 600/407 |
| 2014/0318551 A1 | 10/2014 | Daly | |
| 2015/0223897 A1 | 8/2015 | Kostrzewski et al. | |
| 2015/0282735 A1 | 10/2015 | Rossner | |
| 2016/0249987 A1 | 9/2016 | Hladio et al. | |
| 2018/0036884 A1* | 2/2018 | Chen | A61B 34/30 |

OTHER PUBLICATIONS

Examination Report No. 1 dated Mar. 24, 2022 for Corresponding Australian Patent Application No. 2017323599; 5 Pages.
International Search Report dated Feb. 1, 2018 Issued for Corresponding International PCT Patent Application No. PCT/IB2017/055400 by the Australian Patent Office; 7 Pages.
Extended European Search Report dated Jun. 3, 2020 Issued for Corresponding European Patent Application No. 17848243.6; 10 Pages.

* cited by examiner

SYSTEMS AND METHODS FOR SURGICAL NAVIGATION, INCLUDING IMAGE-GUIDED NAVIGATION OF A PATIENT'S HEAD

CROSS-REFERENCE TO RELATED APPLICATIONS

The present application claims the benefit of U.S. Provisional Patent Application No. 62/384,410, filed Sep. 7, 2016, entitled "Systems and Methods for Surgical Navigation, Including Image-Guided Navigation of a Patient's Head" which is incorporated by reference herein. This application incorporates by reference U.S. Provisional Patent Application No. 62/328,978, filed May 27, 2016, entitled "Systems and Methods to perform image registration and scan 3D surfaces for intra-operative localization", and PCT Patent Application No. PCT/CA2017/000104, filed Apr. 28, 2017 and entitled "Systems, Methods and Devices to Scan 3D Surfaces for Intra-operative Localization."

FIELD

The present application relates to intra-operative localization systems for use in sterile and non-sterile surgical environments and more particularly to systems, methods and devices to track the pose of instruments relative to patient anatomy, to move a camera of an intra-operative localization system from its original mounting position while maintaining a registration between the camera's coordinate-frame and the patient anatomy, to drape an intra-operative localization system to enable use in a sterile environment and to display a visualization of a medical image of the patient anatomy in such environments.

BACKGROUND

Many types of surgery benefit from precise positional navigation of surgical instruments with respect to a patient's anatomy (for example, a patient's head, spine, or joint). For example, in neurosurgery, surgical treatment may include localizing physical lesions identified on a pre-operative image (e.g. MRI) within a patient's brain to perform biopsies, excisions, ablations, etc. For example, in ENT surgery, Functional Endoscopic Sinus Surgery (FESS). Another example is Deep Brain Stimulation (DBS).

SUMMARY

Systems, methods and devices are described herein for performing a navigated surgical procedure involving a patient's anatomy in sterile and non-sterile surgical environments. A camera may be used to determine a registration of the camera coordinate-frame to the patient anatomy or optionally a tracker in relation to the patient anatomy. A drape may be applied to permit use in a sterile surgical environment. The camera may be moved from its original position to enable access to patient anatomy while maintaining a registration of the camera coordinate-frame with the patient anatomy. Alternatively, the camera may be used in a hand-held or head-mounted manner. A visualization of the patient anatomy may be displayed on a computing unit, with visualization reference planes defined by the pose of an instrument or the camera. The visualization may be presented on a display of a computing unit or as part of a head mounted augmented reality system.

There is described a method comprising: releasably coupling a proximal end of a non-sterile camera mounting arm to a surgical clamp immobilizing a patient's anatomy; releasably coupling a non-sterile camera to a distal end of the non-sterile camera mounting arm; following a registration between a coordinate frame of the non-sterile camera and the patient's anatomy in a computing unit: draping the non-sterile camera and the non-sterile camera mounting arm with a camera drape to provide a sterile barrier between the patient's anatomy and the non-sterile camera and non-sterile camera mounting arm; wherein draping is performed without moving a position of the non-sterile camera relative to the patient's anatomy.

The camera drape may be configured to permit the computing unit to use pose data received from the non-sterile camera after the draping with the registration preformed before the draping. The camera drape may be configured to permit a transmission of optical signals to the non-sterile camera without distortion.

Draping the non-sterile camera may comprise enclosing a closed end of a tube-like camera drape over the non-sterile camera, the camera drape extending to cover the non-sterile camera mounting arm.

The method may comprise using a holding mechanism to hold the camera drape in place over the non-sterile camera. The holding mechanism may comprise a shroud that mechanically clips onto the non-sterile camera. The camera drape may comprise a drape optical window and the holding mechanism holds the optical window in a fixed and correct alignment with optics of the non-sterile camera.

The method may further comprise sealing an interface of an open end of the camera drape to a patient drape to maintain a continuous sterile barrier. The patient drape may comprise an opening through which the non-sterile camera mounting arm extends and the interface may be defined by the opening of the patient drape and the open end of the camera drape. The camera drape may comprise a sterile elastic band or an adhesive and the method comprises using the sterile elastic band or adhesive when sealing the interface.

The non-sterile camera may be coupled to the computing unit via a cable and the camera drape encloses a portion of the cable.

The method may comprise rigidly fixing a non-sterile tracker relative to the patient's anatomy to perform the registration; and following the draping, rigidly fixing a sterile tracker relative to the patient's anatomy to perform surgical navigation without performing a second registration. The non-sterile tracker and sterile tracker may be affixed to a same tracker mounting arm having a same position. If a geometry of the non-sterile tracker and a geometry of the sterile tracker are different, a difference may be factored into calculations of poses by the computing unit when the respective non-sterile tracker and sterile tracker are used.

There is disclosed a computer implemented method comprising: performing, in a computing unit, a registration between a coordinate frame of a non-sterile camera and a patient's anatomy, where the non-sterile camera is releasably coupled to a distal end of a non-sterile camera mounting arm and a proximal end of the non-sterile camera mounting arm is releasably coupled to a surgical clamp immobilizing the patient's anatomy and the non-sterile camera communicates pose data to the computing unit; and, following a draping of the non-sterile camera and the non-sterile camera mounting arm by a camera drape to provide a sterile barrier between the patient's anatomy and the non-sterile camera and non-sterile camera mounting arm, where the draping is performed without moving a position of the camera relative to the patient's anatomy: calculating, by the computing unit, poses of sterile instruments relative to the patient's anatomy using the registration to provide surgical navigation during a surgical procedure. The camera drape may be configured to permit a transmission of optical signals to the non-sterile camera without distortion.

The registration may be performed using pose data of non-sterile instruments.

The camera drape may comprise a drape optical window and a holding mechanism may hold the optical window in a fixed and correct alignment with optics of the non-sterile camera.

The method may comprise: receiving at the computing unit pose data from the non-sterile camera of a non-sterile tracker rigidly fixed relative to the patient's anatomy to perform the registration; and following the draping, receiving at the computing unit pose data from the non-sterile camera of a sterile tracker rigidly fixed relative to the patient's anatomy to provide the surgical navigation without performing a second registration. The non-sterile tracker and sterile tracker may be affixed to a same tracker mounting arm having a same position. If a geometry of the non-sterile tracker and a geometry of the sterile tracker are different, a difference is factored into calculations of poses by the computing unit when the respective non-sterile tracker and sterile tracker are used.

The patient's anatomy may be a cranium.

There is disclosed a system to drape a patient, a camera mounting arm and a camera attached thereto to provide a sterile barrier for performing a navigated surgical procedure, the system comprising: a sterile camera drape to cover the camera mounting arm and the camera mounted on a distal end of the camera mounting arm, the sterile camera drape comprising a closed end adjacent the camera when draped and an open end distal from the closed end; and a sealing mechanism to seal the camera drape to a sterile patient drape that covers the patient to maintain a continuous sterile barrier.

The sterile patient drape may provide an opening to receive a proximal end of the camera mounting arm. The open end of the sterile camera drape and the opening of the sterile patient drape may form an interface which is substantially sealed by the sealing mechanism.

The sealing mechanism may comprises a sterile elastic band, the sterile elastic band engaging the camera drape near or at the open end and the sterile patient drape near or at the opening to form the interface.

The sterile elastic band may be affixed to the sterile camera drape near or at the open end.

The sealing mechanism may comprise an adhesive affixed near or at the open end of the sterile camera drape. The adhesive may comprise one or more circumferential adhesive rings comprising an adhesive side and a side affixed near or at the open end of the sterile camera drape, the adhesive side of the one or more circumferential adhesive rings engaging the sterile patient drape near or at the aperture to form the interface.

The sterile patient drape may further comprise: a tubular protrusion with a closed end distal from the sterile patient drape; an adapter near or at the closed end of the tubular protrusion, the adapter comprising a non-sterile connector on a non-sterile side of the sterile patient drape and a sterile connector on a sterile side of the sterile patient drape; where the non-sterile connector is configured to attach to a tracker mounting arm and the sterile connector is configured to attach to a sterile tracker or a sterile tracker mount.

The sterile patient drape may further comprise a tubular protrusion with a closed end distal from the sterile patient drape; and the closed end of the tubular protrusion may be engaged between the sterile tracker and a tracker mounting arm, and the closed end of the tubular protrusion may be sufficiently thin to not significantly affect the position of the sterile tracker attached to the tracker mounting arm.

There is disclosed a computer implemented method comprising the steps of: storing, by a computing unit, the differences between geometries of a non-sterile tracker and a sterile tracker, the non-sterile tracker for use during a non-sterile stage of a surgery for a patient and the sterile tracker for use in place of the non-sterile tracker during a sterile stage of the surgery for the patient; calculating, by the computing unit, a registration of the camera with respect to the non-sterile tracker during the non-sterile stage; during the sterile stage where the sterile tracker is used in place of the non-sterile tracker and the patient is draped with a patient drape, using the registration and differences stored by the computing unit when calculating poses.

The method may further comprise, before the step of calculating the updated registration, the steps of: storing, by the computing unit, a relative position between the non-sterile tracker when mounted to a mounting arm before the patient drape is applied and the sterile tracker when mounted to the mounting arm via the sterile tracker adaptor of the patient drape after the patient drape is applied based on the geometrical properties of the adaptor; during the sterile stage where the sterile tracker is used in place of the non-sterile tracker and the patient is draped with the patient drape, using the relative position stored by the computing unit when calculating poses.

There is disclosed a system for performing a navigated medical procedure, the system comprising: a computer readable storage medium storing instructions which, when executed on a computing unit, configure the computing unit to: capture a first pose between a camera having a first positional relationship with respect to the anatomy of a patient and a tracker having a second positional relationship with respect to the anatomy of the patient; capture a second pose between the camera having a third positional relationship with respect to the anatomy of the patient and the tracker having the second positional relationship; and calculate an updated registration of a camera with respect to the patient's anatomy based on a first registration, the first pose and the second pose.

The system may comprise a camera mounting arm configure to hold the camera in the first positional relationship, and further configured to be positionally adjustable such that the camera is moveable to the third positional relationship.

The system may further comprise the tracker for mounting to have the second positional relationship.

The system may further comprise a tracker mounting arm configured to hold the tracker in the second positional relationship.

The instructions may configure the computing unit to calculate the first registration based on pose data and a medical image of the patient's anatomy.

The instructions may configure the computing unit to provide graphical instructions to a display unit instructing a user to perform at least one of the functions of moving the camera or capturing a pose.

The instructions may configure the computing unit to, after capturing the first pose and before capturing the second pose, provide to a display unit a graphical indication representing the alignment a working volume of the camera with a surgical site.

There is disclosed a computer implemented method comprising the steps: capturing, by the computing unit, a first pose between a camera having a first positional relationship with respect to the anatomy of a patient and a tracker having a second positional relationship with respect to the anatomy of the patient; capturing, by the computing unit, a second pose between the camera having a third positional relationship with respect to the anatomy of the patient and the tracker having the second positional relationship; and calculating, by the computing unit, an updated registration of the camera with respect to the patient's anatomy based on a first registration, the first pose and the second pose.

The method may further comprise the step of calculating, by the computing unit, the first registration based on pose data and a medical image of the patient's anatomy.

The method may further comprise the step of providing, by the computing unit, graphical instructions to a display unit instructing a user to perform at least one of the functions of moving the camera or capturing a pose The method may further comprise, after capturing the first pose and before capturing the second pose, the step of providing, by the computing unit, a graphical indication to a display unit representing the alignment a working volume of the camera with a surgical site.

There is disclosed a system for visualization of a patient's anatomy, comprising: a camera configured to receive optical signals from a tracker having a fixed positional relationship to a patient's anatomy, the optical signals comprising pose data, and to communicate the optical signals to a computing unit; a computer-readable storage device storing instruction which, when executed on the computing unit, configure the computing unit to: provide at least one view of the patient's anatomy based on a medical image of the patient's anatomy to a display unit for display to a user; receive from the camera the optical signals comprising the pose data; calculate, based on the pose data and registration data, the pose of the camera with respect to the patient's anatomy; and modify the view based on camera-based reference planes and the pose of the camera. The tracker may be non-invasively attached to the patient. The camera may be handheld and movements of the camera may cause the computing unit to modify the view. The camera may be head-mounted and head movements may cause the computing unit to modify the view. The display unit may comprise a head-mounted display and the view provided to the display may be overlaid on the user's view of the patient. The display unit may be transparent to permit a user to see through the display unit. The view provided to the display unit may be partially transparent. The system may further comprise a projector for projecting a visible pattern onto the patient's anatomy, the visible pattern corresponding to the camera-based reference planes. The camera based reference planes may comprise one plane perpendicular to an optical axis of the camera and displaced from the camera by a positive distance, d, along the optical axis such that when an area of interest of the patient's anatomy is located at the distance, d, from the camera, the tracker is in view of the camera. The distance, d, may be modified.

There is disclosed a computer implemented method comprising the steps of: providing, by a computing unit, at least one view of a patient's anatomy based on a medical image of the patient's anatomy to a display unit for display to a user; receiving, by the computing unit, optical signals from a camera comprising the pose data of a tracker having a fixed positional relationship with respect to the patient's anatomy; calculating, by the computing unit, based on the pose data and registration data, the pose of the camera with respect to the patient's anatomy; and modifying, by the computing unit, the view based on camera-based reference planes and the pose of the camera.

These and other aspects will be apparent to those of ordinary skill in the art. While some teachings herein may be described with reference to one aspect such as a system (or apparatus), or a method (or process), it will be understood that, as is applicable, equivalent aspects are included herein. For example, when a computer system is disclosed herein, an equivalent computer implemented method is also included, and vice versa. Equivalent computer program products comprising a non-transient medium storing instructions to configure a computer system or perform a computer implemented method are also contemplated for disclosed computer systems (or computing units) and computer implemented methods.

BRIEF DESCRIPTION OF DRAWINGS

Embodiments disclosed herein will be more fully understood from the detailed description and the corresponding drawings, which form a part of this application, and in which.

DETAILED DESCRIPTION

Described herein are systems and methods for performing a navigated surgical procedure involving a patient's anatomy. As the primary example, an image-guided cranial neurosurgical treatment is provided; however, it should be evident that the systems, devices, apparatuses, methods and computer-implemented methods described herein may be applied to any anatomy requiring treatment (e.g. a cranium, a spine, a pelvis, a femur, a tibia, a hip, a knee, a shoulder, or an ankle).

Several systems, methods and devices will be described below as embodiments. The scope of the claims should not be limited by the embodiments set forth in the examples, but should be given the broadest interpretation consistent with the description as a whole.

Reference in the specification to "one embodiment", "preferred embodiment", "an embodiment", or "embodiments" means that a particular feature, structure, characteristic, or function described in connection with the embodiment is included in at least one embodiment, and may be in more than one embodiment. Also, such phrases in various places in the specification are not necessarily all referring to the same embodiment or embodiments.

A computing unit may comprise a laptop, workstation, or other computing device having at least one processing unit and at least one storage device such as memory storing software (instructions and/or data) as further described herein to configure the execution of the computing unit.

Figure 1:
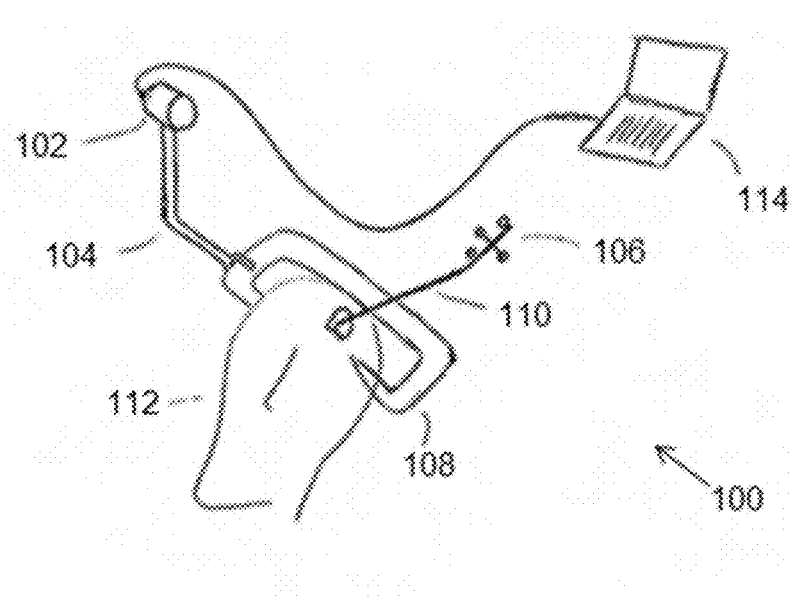
FIG. 1 depicts an intra-operative localization system in the context of a navigated cranial procedure using a camera attached to a head-clamp and a tracker attached to a probe.

FIG. 1 illustrates an exemplary intra-operative localization system 100, in the context of a navigated cranial (brain) procedure. In this intra-operative localization system 100, a camera 102 is shown attached to a mounting arm 104 rigidly mounted to a head-clamp 108, with its field of view oriented towards the site of the surgery. A tracker 106 is attached to an instrument 110 (e.g. a probe), the tracker 106 providing optically detectable features for detection by the camera 102. An instrument may be any type of instrument used in a surgical environment, such as a probe, a tool for cutting or resecting tissue, a tool for retracting tissue, or an imaging too such as an ultrasound probe. The camera 102 transmits camera data (including image data or pose data associated with the tracker 106) to a computing unit 114. The computing unit 114 performs the necessary processing to calculate the position and orientation (pose) of the instrument 110 with respect to the patient's anatomy 112 (i.e. brain), and to display clinically relevant information to the surgeon. The computing unit 114 may also have access to medical image data (such as a magnetic resonance (MRI) image and/or a computed tomography (CT) image of the patient's anatomy, i.e. head/brain), and may further display the navigational information relative to this medical image.

The intra-operative localization system 100 is registered to the patient's anatomy 112; that is, the patient's anatomical planes/axes/features have a relationship, known to the computing unit 114, with respect to the intra-operative localization system 100 coordinate frame.

In operation, the intra-operative localization system is used in three stages (1) pre-operative set-up, (2) patient set-up, registration and planning, and (3) surgical navigation.

Pre-operative setup using the intra-operative localization system 100, includes the following exemplary steps: (a) Non-sterile instruments 110 to be used for registration and planning are calibrated, if necessary; (b) medical image data (e.g. MRI data, CT data) of the patient's anatomy 112 is loaded onto the computing unit 114; (c) registration landmarks are selected, if necessary depending on the method of registration. The pre-operative set-up steps may be performed in advance of entering the operating room. Given the small, portable nature of the exemplary intra-operative localization system 100, the pre-operative steps may be performed by a trained user off-site at any convenient time or location.

Calibrating an instrument 110 generally refers to determining or confirming the spatial relationship between the "effector" of the instrument 110 and the tracker 106 associated with that instrument 110. Various tools/jigs/software routines may be used for instrument 110 calibration. The "effector" of an instrument 110 refers to the aspect of the instrument 110 for which the navigational information is useful. For example: the tip of a biopsy needle; the shaft axis of a probe; the axis, plane, or pattern of a laser; the position and/or orientation of an implantable device.

Patient set-up, registration and planning using the intra-operative localization system 100, includes the following exemplary steps: (a) The patient and intra-operative localization system 100 are brought into the operating room; (b) the patient's anatomy 112 (i.e. head) is immobilized via a head-clamp 108; (c) the camera 102 is mounted to the mounting arm 104 which is in turn connected to the head-clamp 108; (d) landmarks and/or features are localized to generate a registration between the camera coordinate-frame and the patient's anatomy 112 (i.e. head), referred to as Localizer System Registration, and optionally the camera 102 with a medical image of the patient's anatomy 112 (i.e. head), as a mapping between the camera coordinate-frame and the coordinate-frame of the medical image or model, referred to as Image Registration. The term "registration" generally refers to at least Localizer System Registration, but may also include Image Registration when required; (e) the registration is verified (e.g. a check to ensure that a virtual spatial representation of a tracked instrument 110 relative to the patient's anatomy 112 (i.e. head) matches the physical spatial relationship between the tracked instrument 110 and the patient's anatomy 112 (i.e. head); (f) the surgical intervention is planned by, for example, identifying the location of a craniotomy that would provide an optimal path towards a lesion to be resected and/or biopsied.

Surgical navigation using the intra-operative localization system 100, includes the following exemplary steps during sterile surgical procedures: (a) the patient is prepped and draped; (b) the camera 102 is draped without moving its position relative to the patient's anatomy 112 (i.e. head); (c) the sterile instruments 110 (e.g. a probe connected to a tracker 106) are calibrated. Surgical navigation, regardless of whether it is sterile or non-sterile, includes the step of calculating the pose of at least one instrument 110 and displaying a representation of that instrument 110 on the computing unit 114 in relation to a medical image of the patient's anatomy 112 (i.e. head). Optionally, further registration verifications may be performed to check if the patient's position relative to the camera 102 of the intraoperative localization system 100 is accurate.

Figure 2:
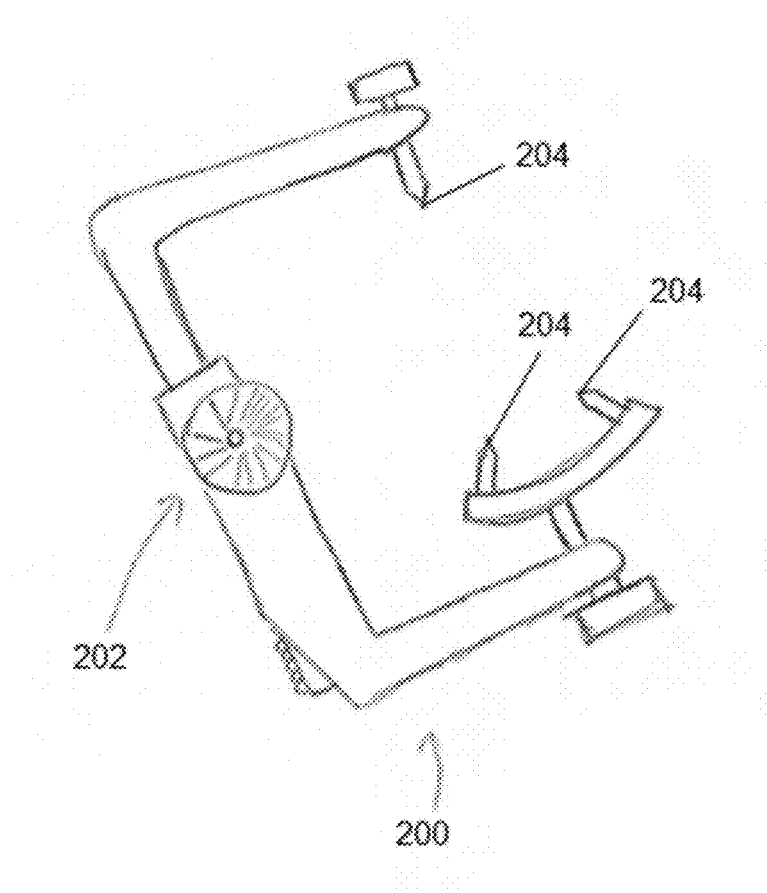
FIG. 2 depicts a head-clamp with a starburst mechanism connector.

A head-clamp 108 may be any type of clamp for restricting the movement of the patient's head. FIG. 2 illustrates an exemplary head-clamp 200 in the form of a Mayfield-style clamp, which immobilizes a patient's skull by clamping it with three points of fixation 204. The head-clamp 200 may include a connector 202 to connect the head-clamp 200 to an operating table and optionally other mounting arms. The connector 202 of the head-clamp 200 may be any form of connector. The exemplary connector depicted in FIG. 2 is a starburst mechanism. A starburst mechanism is advantageous for rigid connections, since it allows rotational adjustment at the time of connection, but when secured, provides a highly rigid structure that is unlikely to shift when forces or impacts are applied.

Figure 3:
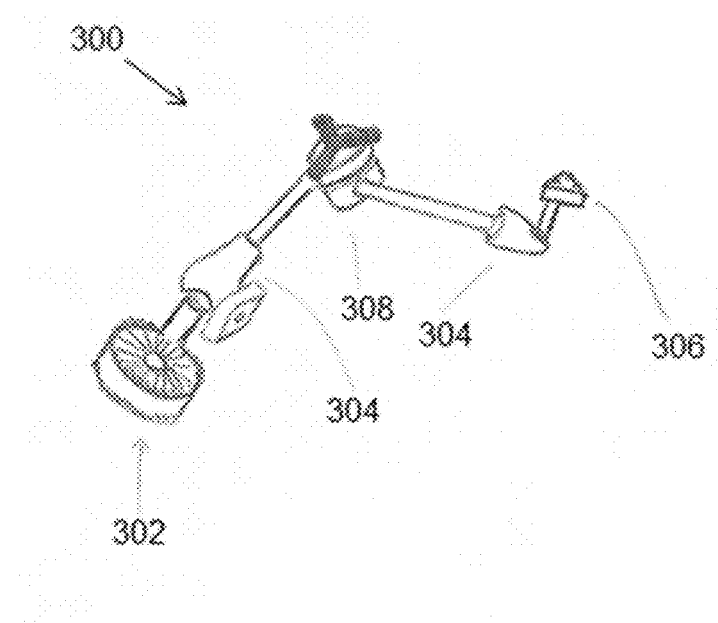
FIG. 3 depicts a mounting arm with a starburst mechanism connector.

With reference to FIG. 3, in one embodiment, a mounting arm 300 is provided, the mounting arm 300 configured to mount to a head-clamp 108, and thus provide a rigid reference to the patient's anatomy 112 (i.e. the skull, head-clamp 108 and mounting arm 300 have a rigid and fixed positional relationship). The mounting arm 300 comprises a camera mount 306 connected to the arm mechanism allowing for positional alignment of the camera 102. The mounting arm 300 may provide a complementary connector 302 to the head-clamp connector 202. The complementary connector 302 to may any form of connector. The exemplary complementary connector 302 depicted in FIG. 3 is a complementary starburst mechanism.

The connector 302 on the mounting arm 300 is used to rigidly attach to the head-clamp 108, and may optionally provide an additional connector interface, such as the same starburst interface, for further attachment thereto (e.g. to attach to the operating table, or to attach a second mounting arm 300). The mounting arm 300 is preferably adjustable, such that the camera's working volume may be aligned with the working volume of the surgical instruments 110, referred to as the surgical site. This may be achieved by providing up to 6 Degrees of Freedom (DOF) positional adjustment in the mounting arm 300 with respect to the patient's anatomy 112 (i.e. head). The mounting arm 300 may incorporate any mechanism to achieve positional alignment. The exemplary embodiment in FIG. 3 depicts a starburst-style connector 302 which provides 1 DOF; an angular joint 308 provides another DOF; two ball joints 304 provide multiple degrees of freedom each; in aggregate, this exemplary embodiment of a mounting arm 300 provides 6DOF of positional alignment.

Once aligned in the desired orientation with respect to the surgical site, the mounting arm 300 must be rigidly locked in place. This may be accomplished via various mechanisms, including lockable ball joints 304, lockable angular joints 308, lockable gooseneck mechanisms, or any other form moveable and rigidly lockable mechanism. Knobs may be provided so that the user can lock the mounting arm in place.

Figure 4:
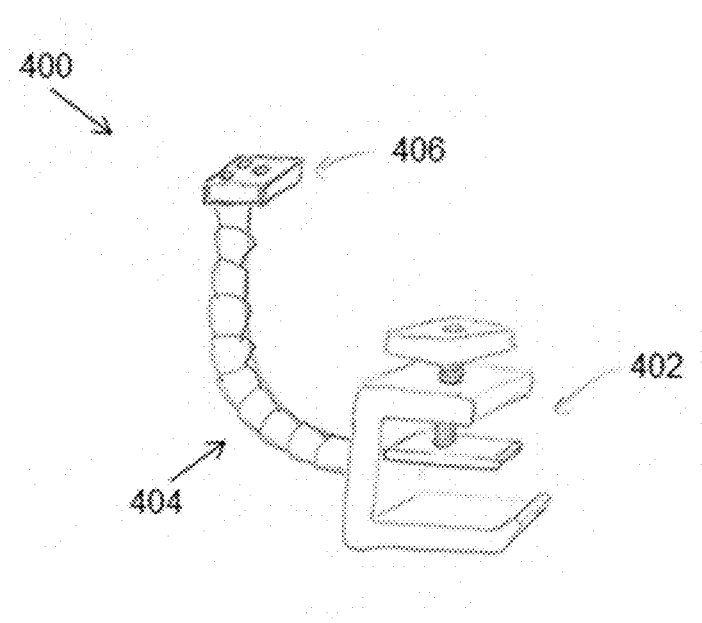
FIG. 4 depicts an alternative mounting arm with a gooseneck mechanism.

With respect to FIG. 4, an alternate goose-neck mounting arm 400 that is also capable of 6DOF of positional alignment is depicted. The exemplary embodiment of the goose-neck mounting arm 400 comprises a camera and/or tracker mount 406 connected to a "goose-neck" arm mechanism 404 that allows 6DOF positional alignment, which is in turn connected to a clamp 402 to rigidly connect the goose-neck mounting arm to the operating table, the head-clamp 108, or any other surface of the surgical environment.

The exemplary mounting arm 300 and alternative gooseneck mounting arm 400 may be adapted to attach to a tracker instead of a camera.

Figure 5:
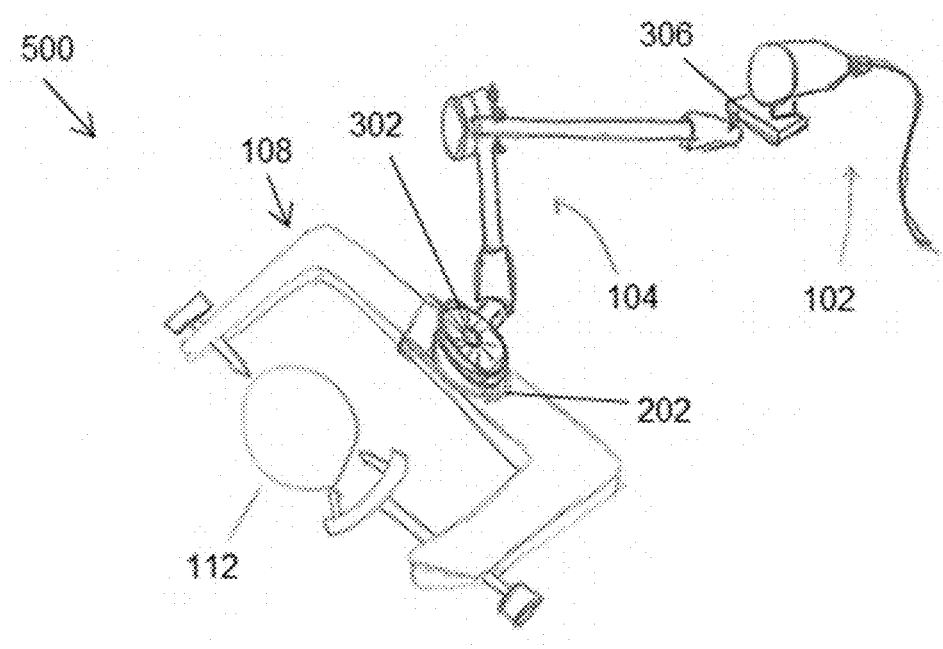
FIG. 5 depicts a camera-head-clamp assembly where a camera is mounted to a head-clamp.

FIG. 5 depicts an exemplary camera-head-clamp assembly 500 comprising the head-clamp 108 holding a patient's anatomy 112 (i.e. head), mounting arm 104 and camera 102, where the camera 102 is generally oriented toward the patient's anatomy 112 (signifying the alignment of the camera's working volume with the surgical site).

The camera 102 may be rigidly fixed to the mounting arm 104 via a camera mount 306, which provides a rigid attachment mechanism fixing the camera 102 to the mounting arm 104. Rigid mechanisms connecting the camera 102 to the mounting arm 104 may include camera 102 being permanently attached to the mounting arm 104 (e.g. by being integrally formed, via welding, adhesion, or fastening), cam locks, threaded connectors, dovetail connections, or magnetic connectors. The rigid mechanism of the camera mount 306 holds the camera 102 in a fixed position relative to the mounting arm 104 at least for the duration of the surgically navigated portion of the procedure. Alternatively, a releasable and repeatable connection is also contemplated, such that the camera 102 may be removed from the camera mount 306 of the mounting arm 104 (e.g. for convenience), and re-attached in the exact same position. Any highly repeatable connection mechanism is contemplated for this purpose, including magnetic kinematic mounts. The camera mounting arm 104 is connected to the head-clamp 108 via the connector 202 of the head-clamp 108 being connected to the complimentary connector 302 of the mounting arm 104.

Figure 6:
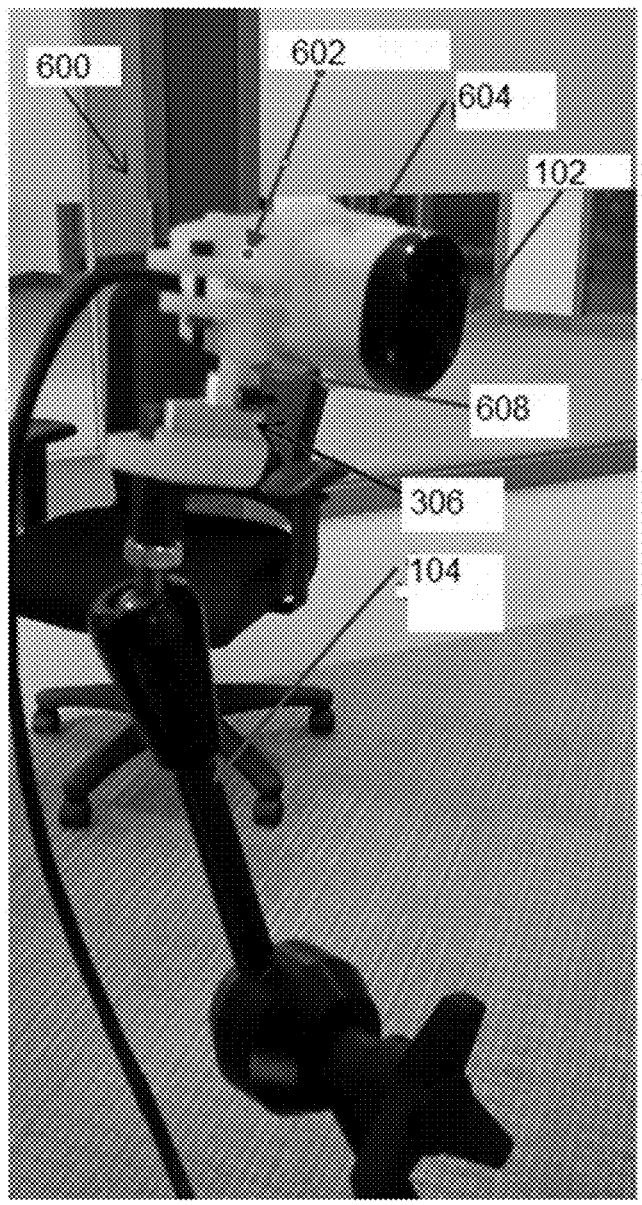
FIG. 6 shows a camera-mounting arm assembly where a camera is mounted to a camera mounting arm.

FIG. 6 shows an exemplary camera-mounting arm assembly 600 (similar to the assembly 500 of FIG. 5) but where a camera 102 is mounted to a mounting arm 104 via a camera clamp 602 (the clamp 602 having an upper portion and a lower portion, a threaded adjustment mechanism and a hinge joint, such that the threaded adjustment mechanism can apply sufficient force to the camera 102 to rigidly hold it in place, the clamp 602 further having a camera mount 608 comprised of a force-applying feature (e.g. magnet(s)) and kinematic locating features (in this case, mating hemispherical features and v-slots)). The mounting arm 104 provides a complementary and mating camera mount 306. The result is that (a) the camera 102/clamp 602 can be attached to the mounting arm 104 via camera mount 306; (b) the camera 102/clamp 602 can be removed from the mounting arm 104 by pulling it off the camera mount 306, and (c) b) the camera 102/clamp 602 can be reattached with the exact same positional relationship to the mounting arm 104 via the camera mount 306. The camera 102 includes features 604 configured to optionally connect a shroud. Features 604 may be a raised surface from the shape of the camera body (such as is shown) or an indentation (not shown) or a combination of same for receiving a cooperating surface of the shroud.

In some embodiments, it may be desirable to either have a non-fixed camera location, or to have the ability to move or reposition the camera 102 relative to the surgical site. In order to facilitate these options, the system may include a tracker with a fixed and rigid positional relationship with respect to the head-clamp 108, for example, via a mounting arm for the tracker.

Figure 7:
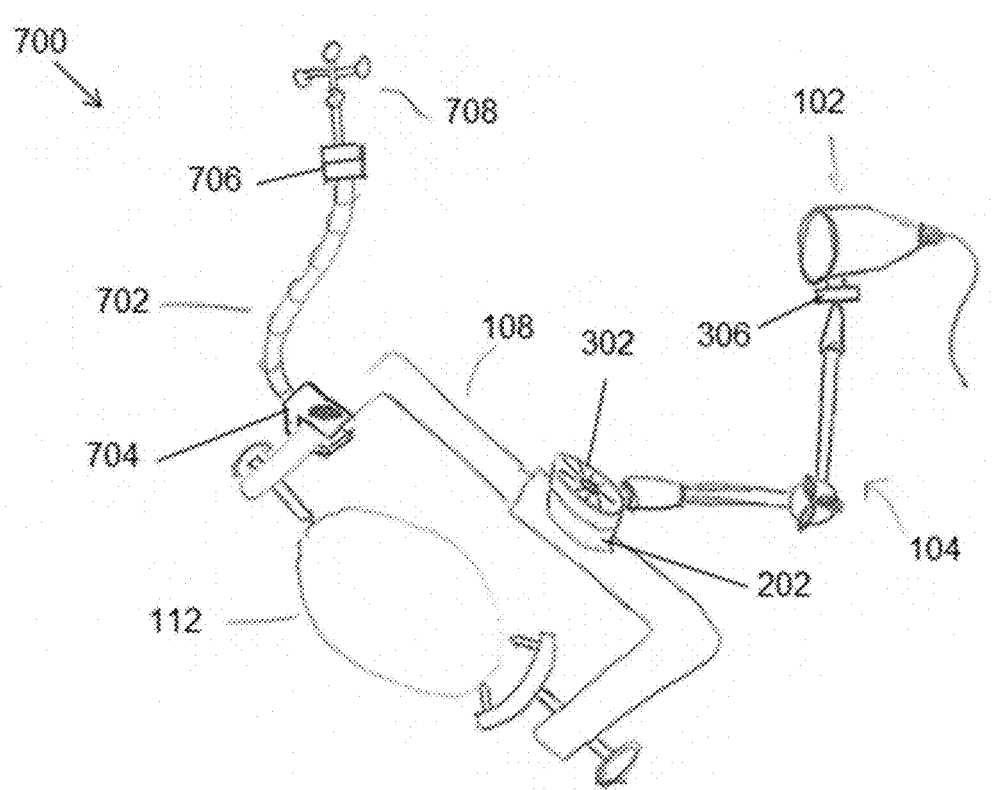
FIG. 7 depicts a camera-tracker-head-clamp assembly where a camera and a tracker are mounted to a head-clamp.

For example, FIG. 7 camera-tracker-head-clamp assembly 700 shows both a camera 102 and tracker 708 mounted to a head-clamp 108 restricting the movement of the patient's anatomy 112 (i.e. head). The camera 102 may be mounted to the camera mounting arm 104 via the camera mount 306. The camera mounting arm 104 may be connected via a connector 302 to a complementary head-clamp connector 202. The camera 102 may be oriented toward the surgical site, and the tracker 708 is preferably fixed in a position that is within the working volume of the camera 102 (i.e. the tracker 708 is in close proximity to the surgical site, and generally orientated such that it is within the working volume of the camera 102). The tracker 708 may be rigidly attached to the head-clamp 108 in a permanent manner (for the duration of the procedure). For example, the tracker 708 may be integrally formed with its own mounting arm 702 which is in turn connected to the head-clamp 108 via, for example, a clamp 704. The tracker 708 may also be releasably and repeatably coupled to the tracker mounting arm 702 (with a high degree of positional repeatability) via a tracker mount 706. When rigidly attached to the mounting arm 702/head-clamp 108, the tracker 708 serves as a rigid reference for the patient's anatomy 112, and the camera 102 need not maintain a rigid and fixed position with respect to the patient's anatomy 112. As described further herein, software in computing unit 114 may be configured to perform a registration so as to register the positional relationship between the tracker 114 and the patient's anatomy 112 and thereafter track the pose of the patient's anatomy 112 in the field of view (working volume) of the camera 102 even if the camera 102 is in a position that is different from the camera's position at registration. Exemplary benefits of this configuration include the ability to adjust the camera's 102 position mid-procedure (e.g. to attain a better viewing angle of the surgical site) and the ability to mount the camera 102 on other objects other than the patient's anatomy 112 such as a cart, the operating table (via standard operating table attachment rails), or using the camera 102 in a hand-held or surgeon-mounted (e.g. head mounted) manner.

Figure 8:
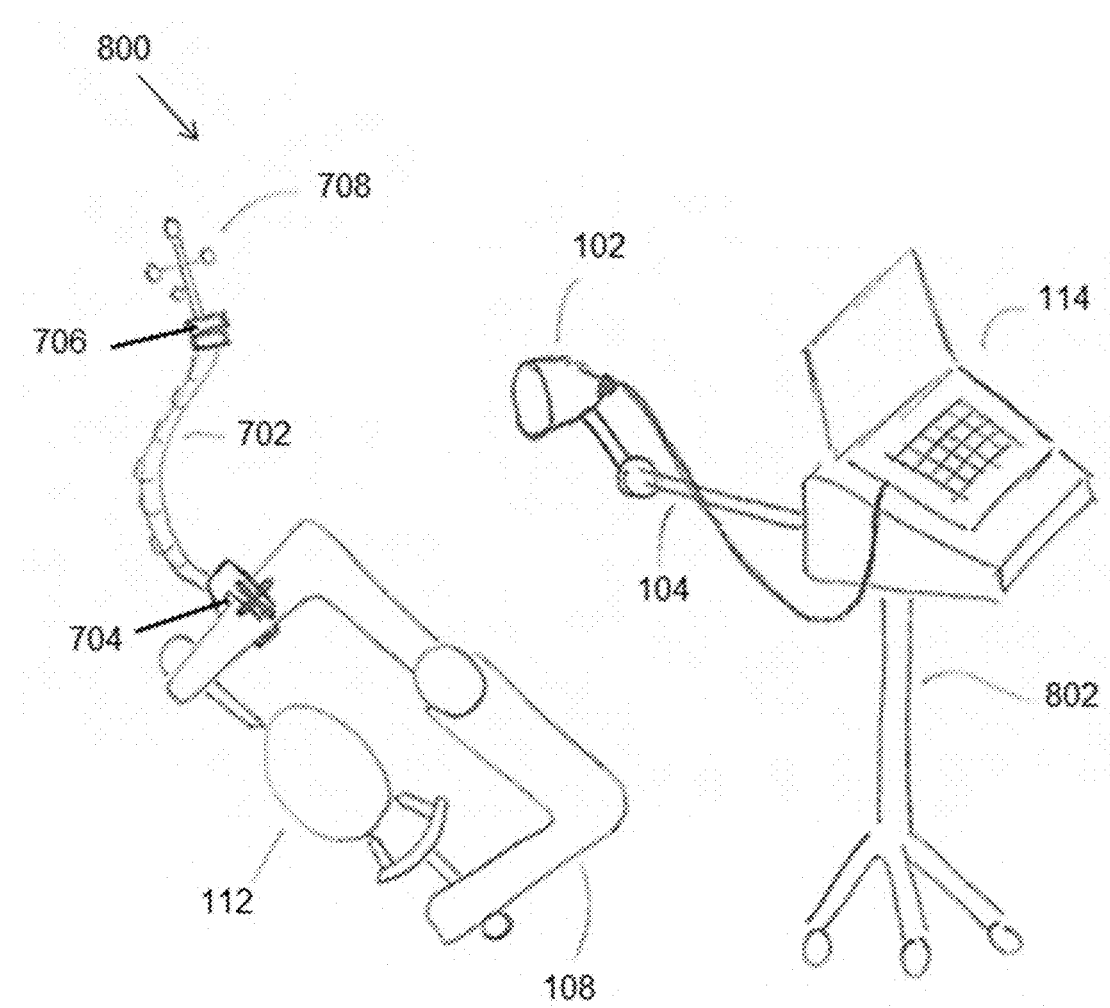
FIG. 8 depicts an intra-operative localization system where a tracker mounted to a head-clamp and a camera separately mounted to a cart.

FIG. 8 illustrates an exemplary intra-operative localization system 800 where the camera 102 is rigidly attached to a cart 802 providing the computing unit 114. The camera 102 is mounted to a mounting arm 104 which is in turn rigidly connected to the cart 802. A head-clamp 108 restricts the movement of the patient's anatomy 112. A tracker 708 is mounted via a tracker mount 706 to a tracker mounting arm 702, which is in turn rigidly connected to the head-clamp 108 via, for example, a clamp 704.

Patient and Camera Drapes for Sterile/Non-Sterile Use

Figure 9:
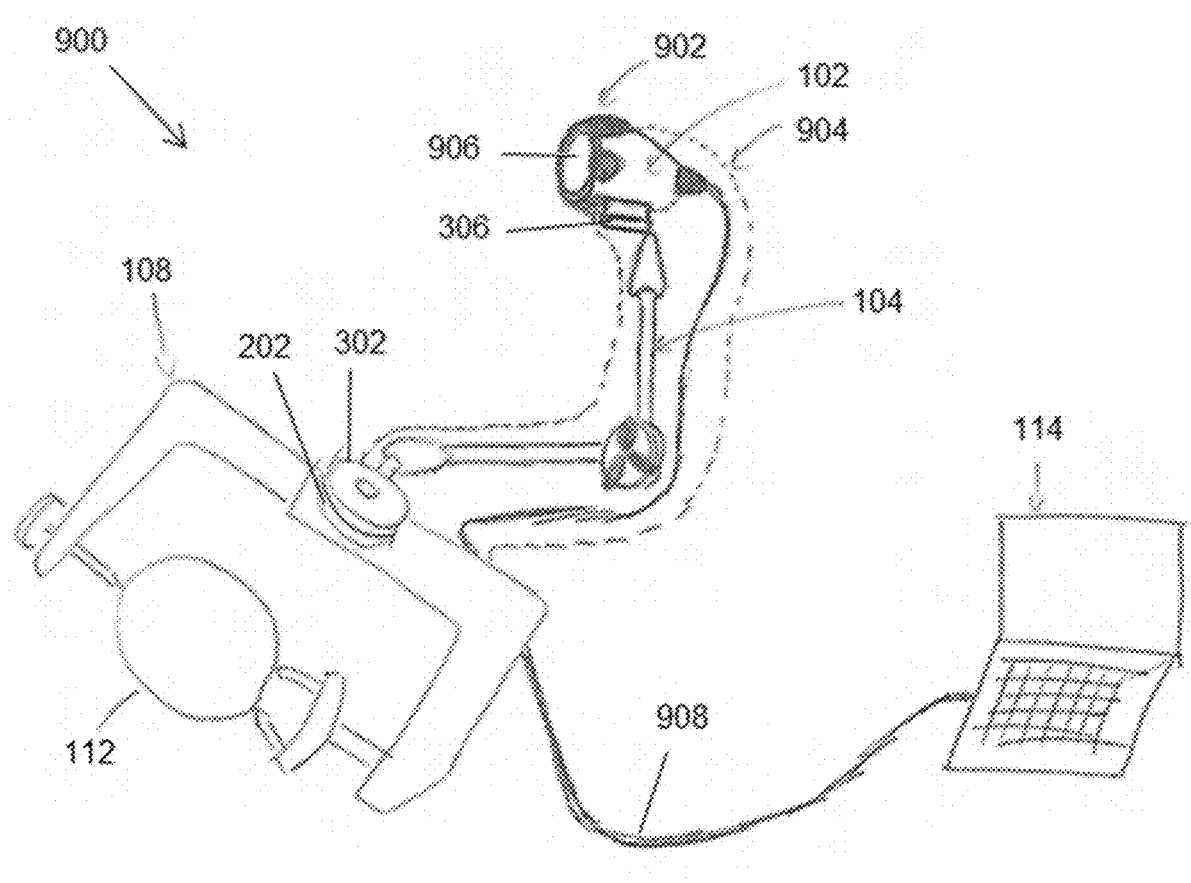
FIG. 9 depicts a sterile draped intra-operative localization system with a camera drape.
Figure 10:
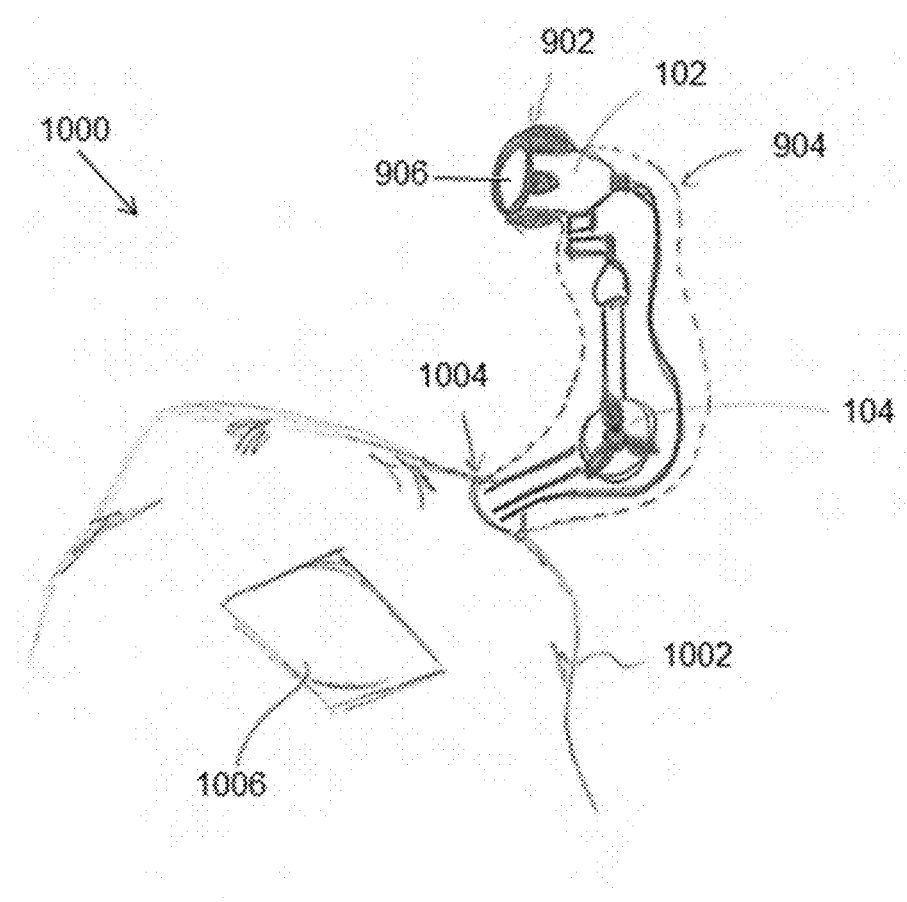
FIG. 10 depicts a sterile draped intra-operative localization system with a camera drape and patient drape.
Figure 11:
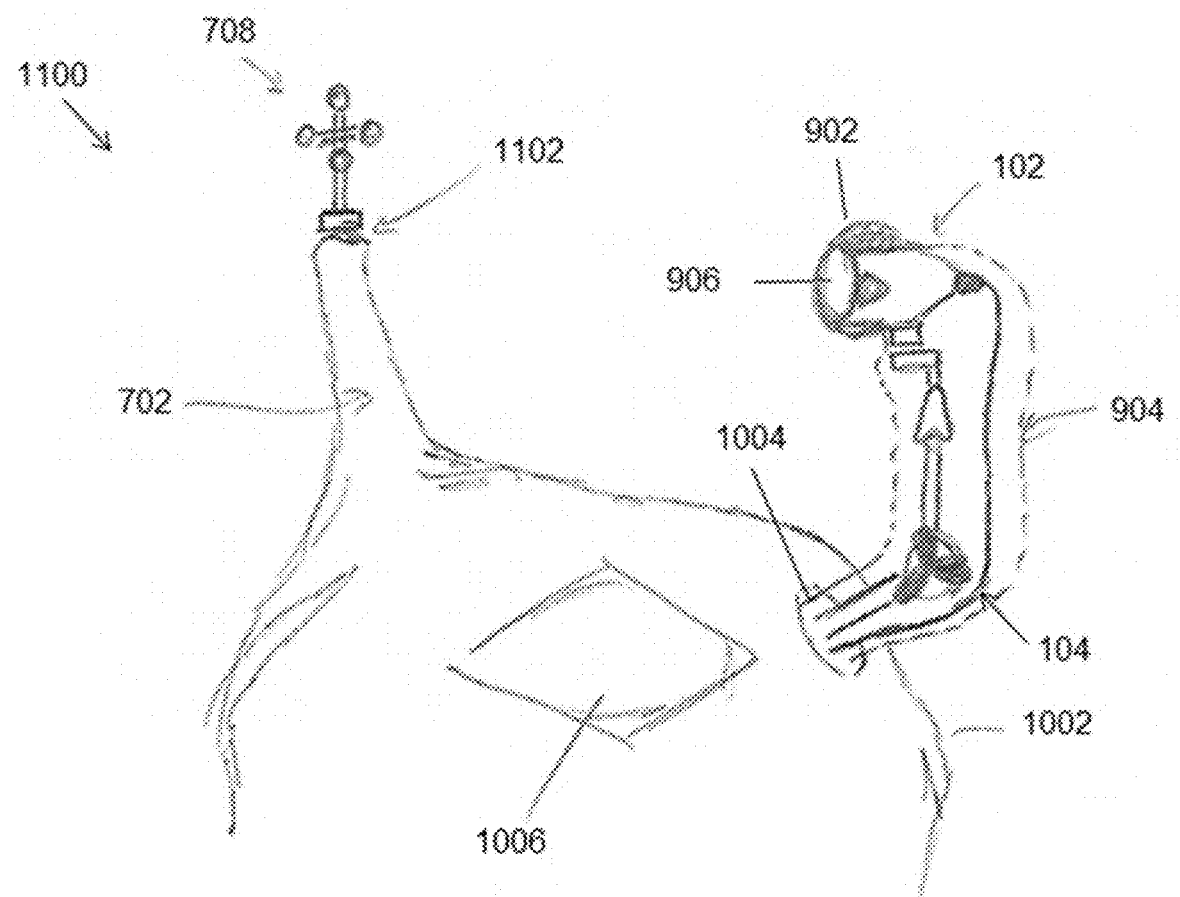
FIG. 11 depicts a sterile draped intra-operative localization system with a camera drape, a patient drape and a tracker mounted to a mounting arm under the patient drape without breaking the sterile barrier.

With reference to FIGS. 9-11, it is desirable to use an intra-operative localization system in a sterile surgical procedure. FIG. 9 depicts an exemplary sterile draped intra-operative localization system 900. In exemplary intra-operative localization system 900, a camera 102 is attached to a mounting arm 104 via a camera mount 306. Camera 102 is enclosed in a sterile drape 904 affixed to the camera 102 via a shroud 902. The drape 904 extends to the base of the mounting arm 104 near a mounting arm connector 102 which attaches the mounting arm 104 to the head-clamp 108 at a head-clamp connector 202. The head-clamp 108 restricts the motion of the patient's anatomy 112 (i.e. head). The camera 102 is connected via a cable 908 to the computing unit 114.

In the exemplary embodiment, the intra-operative localization system 900 includes a sterile drape 904 with an optical window 906 at its distal end. The drape 904 includes a long tube-like body that encloses the camera 102, a proximate portion of the cable 908 connecting the camera 102 to the computing unit 114 and the mounting arm 104. The drape 904 may terminate at the base of the mounting arm 104, which may be located at its connector 302 (i.e. the attachment point to the connector 202 of the head-clamp 108). The proximate portion of the cable is typically at least the portion of the cable that extends from the camera to (more or less) a length of the mounting arm 104. This length should provide sufficient freedom to move the mounting arm 104 without impacting sterility requirements. A slightly longer or shorter length may also function similarly. The drape 904 is intended to cover the portion of the cable that may come into contact with personnel or tools (during the surgery when sterility is to be maintained) at or about the location of the surgery near the patient's head.

The exemplary intra-operative localization system 900 provides a mechanism to hold the drape 904 in place on the camera 102. This is desired in order to hold the drape window 906 in alignment with the optics of camera 102 (e.g. glass or other material about the lens opening (not shown)), or the optical path. This mechanism may be a shroud 902, that mechanically clips, or otherwise connects, to the camera 102 via the shroud connecting features 604 of the camera 102 while holding the drape window 906 in a fixed and correct alignment with the camera's optics, without puncturing or compromising the sterile barrier (i.e. by sandwiching the sterile drape 904 between the body of the shroud 902 and the camera 102). The shroud 902 may be capable of deflecting, such that the shroud 902 provides a spring force to hold the camera 102 and the drape 904 assembly together. The shroud 902 may provide locating features intended to mate with complementary locating features on the camera 102, to enforce the correct alignment between the shroud 902 and the camera 102. The drape window 906 is designed to allow for undistorted transmission of optical signals; it may be constructed of a rigid, thin and flat optically transparent material.

With reference to FIG. 10, in a further illustration, the sterile draped intra-operative localization system 1000 is similar to system 900 and is used where the patient is also draped for the surgical procedure. The camera 102, shroud 902, mounting arm 104, head-clamp 108 (not shown), camera drape 904 and drape window 906 may be arranged as described above for the exemplary localization system 900 depicted in FIG. 9. In the present embodiment, a patient drape 1002 covers the patient and the head-clamp 108. The patient drape 1002 has an opening 1006 to expose the surgical site of the patient's anatomy 112 (i.e. head). The patient drape 1002 further provides a mounting arm 104 opening 1004 such that the camera 102 and mounting arm 104 covered by a camera drape 904 can stick out through the patient drape 1002. The draping procedure is performed according to aseptic techniques.

The interface between the patient drape 1002 and the camera drape 904 may be substantially sealed to maintain a continuous sterile barrier. To maintain this barrier, the sterile patient drape 1002 and camera drape 904 may be configured in the following ways. A sterile elastic band may be used to hold the patient drape 1002 opening tightly around the camera 102 drape 904. The elastic band may be provided in the sterile packaging of the sterile patient drape 1002 and camera drape 904 as a separate unit. Alternatively, the elastic band may be pre-attached to the camera drape 904 or patient drape 1002. The camera drape 904 may comprise one or multiple circumferential rings (or a spiral) with adhesive at or near the end of the camera drape 904 (distal from the window end) such that the patient drape 1002 can be adhered to the camera drape 904 along the outer circumference of drape 904. The adhesive rings may be covered by strips, and exposed for use by removing the adhesive strip covering. Multiple circumferential adhesive rings may be provided so that the desired location along the length of the patient drape 1002 and the camera drape 904 interface may be used. The camera drape 904 may provide an adhesive strip, either partially or removably attached thereto. The adhesive strip may be used to secure the camera drape 904 to the patient drape 1002. Other fasteners may be contemplated, including hook and eye, pull fasteners, etc. configured to maintain the sterile barrier.

With reference to FIG. 11, in certain surgically-navigated procedures, it may be desirable to use the intra-operative localization system 100 in non-sterile as well as sterile environments in the same procedure. For example, in neurosurgical applications, it may be desirable to perform registration (i.e. localization system registration and/or image registration) prior to the establishment of the sterile field because the registration landmarks are non-sterile.

FIG. 11 depicts a sterile draped intra-operative localization system 1100. The exemplary intra-operative localization system 1100 is conducive to sterile and non-sterile use within the same procedure, since it is configured to be used with or without the sterile camera drape 190. The sterile camera drape 904 may be applied to the camera 102 and/or mounting arm 104 without moving the camera 102 relative to the patient's anatomy 112 such that the position of the camera 102 is the same while the surgical environment is not sterile and after the draping techniques have been applied to make the surgical environment sterile. When the exemplary intra-operative localization system 1100 is used in sterile use, it may be necessary to use only sterile instruments 110 in order to maintain the sterile environment. Conversely, when the exemplary intra-operative localization system 1100 is used in non-sterile use, it may be acceptable to use non-sterile instruments 110 (such as non-sterile registration instruments 110).

As previously described, it is advantageous to have a tracker 708 rigidly fixed relative to the patient's anatomy 112 (i.e. head). It may be desirable to have a tracker 708 rigidly fixed relative to the patient's anatomy 112 in a sterile environment. In the exemplary embodiment depicted in FIG. 11, a sterile tracker 708 is rigidly attached to the head-clamp 108 through the patient drape 1002. The patient drape 1002 includes a window 1006 to make visible the patient anatomy 112. The sterile tracker 708 is connected to a non-sterile tracker mount 1102 through the patient drape 1002 without compromising sterility. The patient drape 1002 may include an adaptor with a non-sterile-side connection for attachment to the tracker mounting arm 702, and a sterile side for attachment to the sterile tracker 708 and/or the sterile tracker mount 1102. The geometrical properties of the adaptor may be known to the computing unit 114, such that the relative position between a non-sterile tracker 708 (when mounted to the tracker mounting arm 702 before the patient drape 1002 is applied) and a sterile tracker 708 (when mounted to the tracker mounting arm 702 after the patient drape 1002 is applied) is known to the intra-operative localization system 1100. Additionally, the location of the optically detectable features of the tracker 708 may also be known.

The sterile tracker 708 may also be configured to puncture the patient drape 1002 and attach to the tracker mounting arm 702 and/or the tracker mount 1102, the punctured part of the patient drape 1002 being covered by the base of the tracker 708 such that contamination to the sterile side of the patient drape 1002 is highly improbable.

The patient drape 1002 may be sandwiched between the sterile tracker 708 and the tracker mounting arm 702, the patient drape 1002 being sufficiently thin so as to not significantly affect the position of the sterile tracker 708 on the tracker mounting arm 702 and allow a sufficiently strong connection between the sterile tracker 708 and the tracker mounting arm 702 to not allow the sterile tracker 708 to fall off the tracker mounting arm 702 due to movement of the patient drape 1002 during the surgical procedure.

The intra-operative localization system 1100 may use a sterile tracker 708 and a non-sterile tracker 708 at different stages of a surgical procedure. The sterile tracker 708 may have the same geometry as the non-sterile tracker 708; alternatively, the respective geometries may be different, in which case the difference may be known to the computing unit 114 and be factored into calculations of poses at different stages of a surgical procedure accordingly.

The camera 102, camera mounting arm 104, camera drape 904, camera drape window 906 and shroud 902 may be configured similar to the above described sterile draped camera intra-operative localization system 1000. The camera mounting arm 104 protrudes from the camera mounting arm opening 1004. The camera 102 may provide a user interface (comprising for example buttons, indicator lights and/or displays). The intra-operative localization system 1100 may allow the user to access to the user interface both when sterile and non-sterile. When the camera drape 904 has been applied and the surgical environment is sterile, the user interface may be accessible and/or functional through the sterile camera drape 904. This may be accomplished, for example, by the camera drape 904 being of clear and flexible material.

Figure 12:
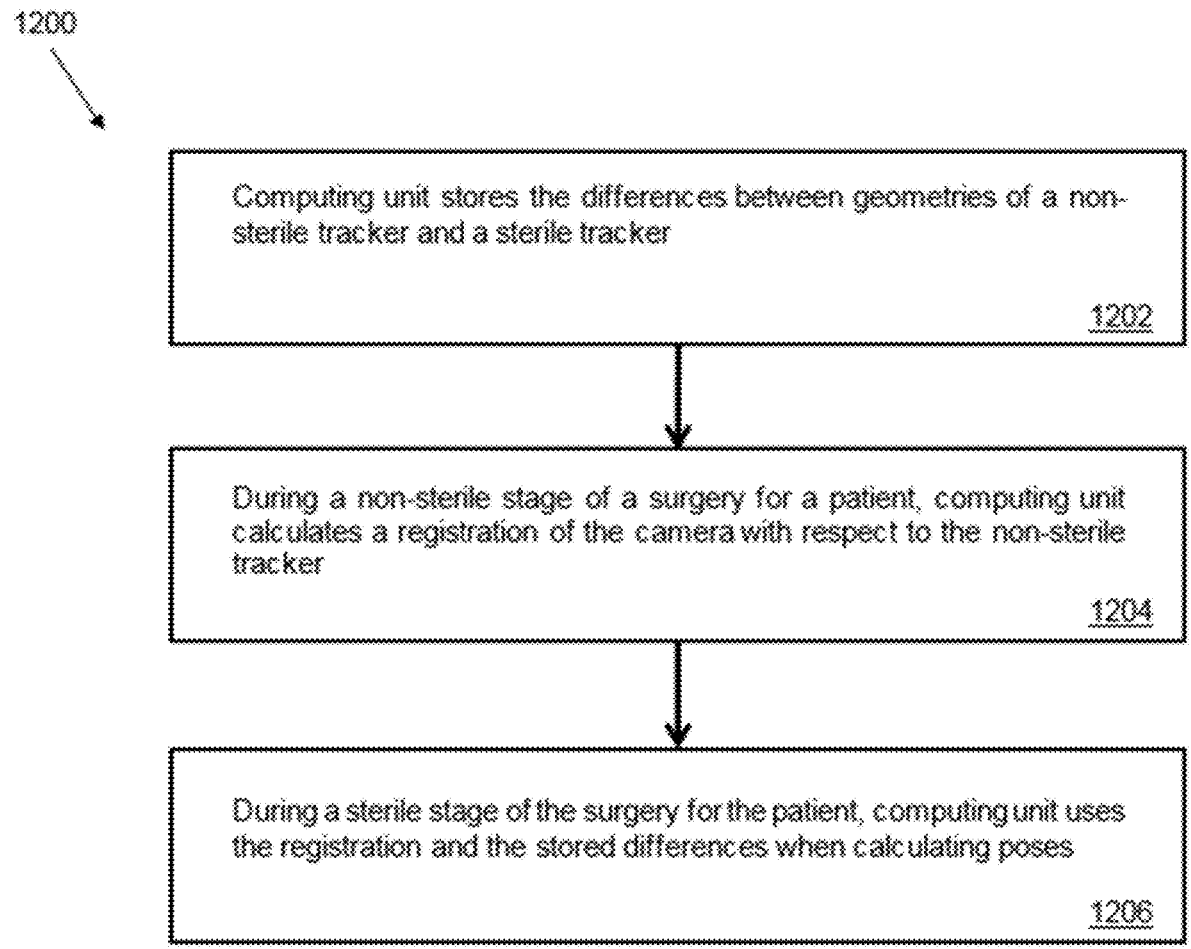
FIG. 12 depicts a computer implemented method for storing differences in geometries of a sterile tracker and a non-sterile tracker and using a registration between a camera and the non-sterile tracker and the stored differences when calculating poses during a sterile stage of a surgery for a patient.

Reference is now made to FIG. 12 depicting a computer-implemented method 1200 for storing differences in geometries of a non-sterile tracker 708 and a sterile tracker 708 and using a registration between a camera 102 and the non-sterile tracker 708 and the stored differences when calculating poses during a sterile stage of a surgery for a patient. A computing unit 114 stores (at 1202) the differences between geometries of a non-sterile tracker 708 and a sterile tracker 708, the non-sterile tracker 708 for use during a non-sterile stage of a surgery for a patient and the sterile tracker 708 for use in place of the non-sterile tracker 708 during a sterile stage of the surgery for the patient. The computing unit 114 calculates (at 1204) a registration of the camera 102 with respect to the non-sterile tracker 708 during the non-sterile stage. During the sterile stage where the sterile tracker 708 is used in place of the non-sterile tracker 708 and the patient is draped with a patient drape 1002, the computing unit 114 (at 1206) uses the registration and differences stored by the computing unit 114 when calculating poses.

In one embodiment, the computing unit 114 may store a relative position between the non-sterile tracker 708 when mounted to a mounting arm 702 before the patient drape 1002 is applied and the sterile tracker 809 when mounted to the mounting arm 702 via the sterile tracker adaptor of the patient drape 1002 after the patient drape 1002 is applied, based on the geometrical properties of the adaptor. During the sterile stage where the sterile tracker 708 is used in place of the non-sterile tracker 708 and the patient is draped with the patient drape 1002 the computing unit 114 may use the stored relative position when calculating poses.

"Move Camera" Function

It may be desirable to reposition the camera 102, for example, in order to achieve better viewing angles of the instruments 110 being tracked as part of the surgical procedure. However, where the camera 102 is rigidly mounted to the head-clamp 108, the positional relationship between the camera 102 and the patient's anatomy 112 may be registered and moving the camera 102 would compromise this registration.

A system is described herein to provide a "Move Camera" function, allowing the camera 102 to be moved between a plurality of positions and orientations while maintaining a registration that allows the position and orientation of instruments 110 to be tracked relative to the patient's anatomy 112.

After mounting the camera 102 to the patient anatomy 112 to generate a camera-patient anatomy registration which is stored in the memory of a computing unit 114, the camera 102 may be repositioned without compromising the registration using the following system. A tracker 708, either sterile or non-sterile, is rigidly attached to the head-clamp 108 and is within the field of view and trackable by the camera 102. Computing unit 114 captures a first pose of the rigidly-mounted tracker 708 relative to the camera 102 and the patient anatomy 112, and computes a tracker-patient anatomy registration (i.e. a registration between the coordinate-frames of the tracker 708 and the patient's anatomy 112) based on this initial pose, and stores this tracker-patient anatomy registration in the memory of the computing unit 114. The camera 102 may now be repositioned to a desired alignment with the surgical site subject to the rigidly-mounted tracker 708 remaining trackable within the field of view and working volume of the camera 102. The computing unit 114 captures a second pose of the rigidly-mounted tracker 708 relative to the camera 102 and the patient anatomy 112 and computes a new camera-tracker registration (i.e. the registration between the coordinate-frame of the camera 102 in its new position and orientation with the coordinate-frame of the rigidly-mounted tracker 708) which is then used by the computing unit 114 to compute a new camera-patient anatomy registration (i.e. the registration between the coordinate-frame of the camera 102 in its new position and orientation with the coordinate-frame of the patient anatomy 112) by applying the tracker-patient anatomy registration stored in the memory of the computing unit 114 to the new camera-tracker registration.

The memory of the computing unit 114 may include instructions to display to a user describing how to capture the poses of the camera 102 and to compute the registrations accordingly. The computing unit 114 may also display graphical instructions to the user on a display of the computing unit 114 to guide them through the aforementioned steps.

The computing unit 114 may be further configured to display a graphical indication of how the camera's working volume aligns with the surgical site, after capturing the first pose and before capturing the second pose (i.e. to give a user visual feedback to help them align the camera to a location that has an improved view of the surgical site).

Figure 13:
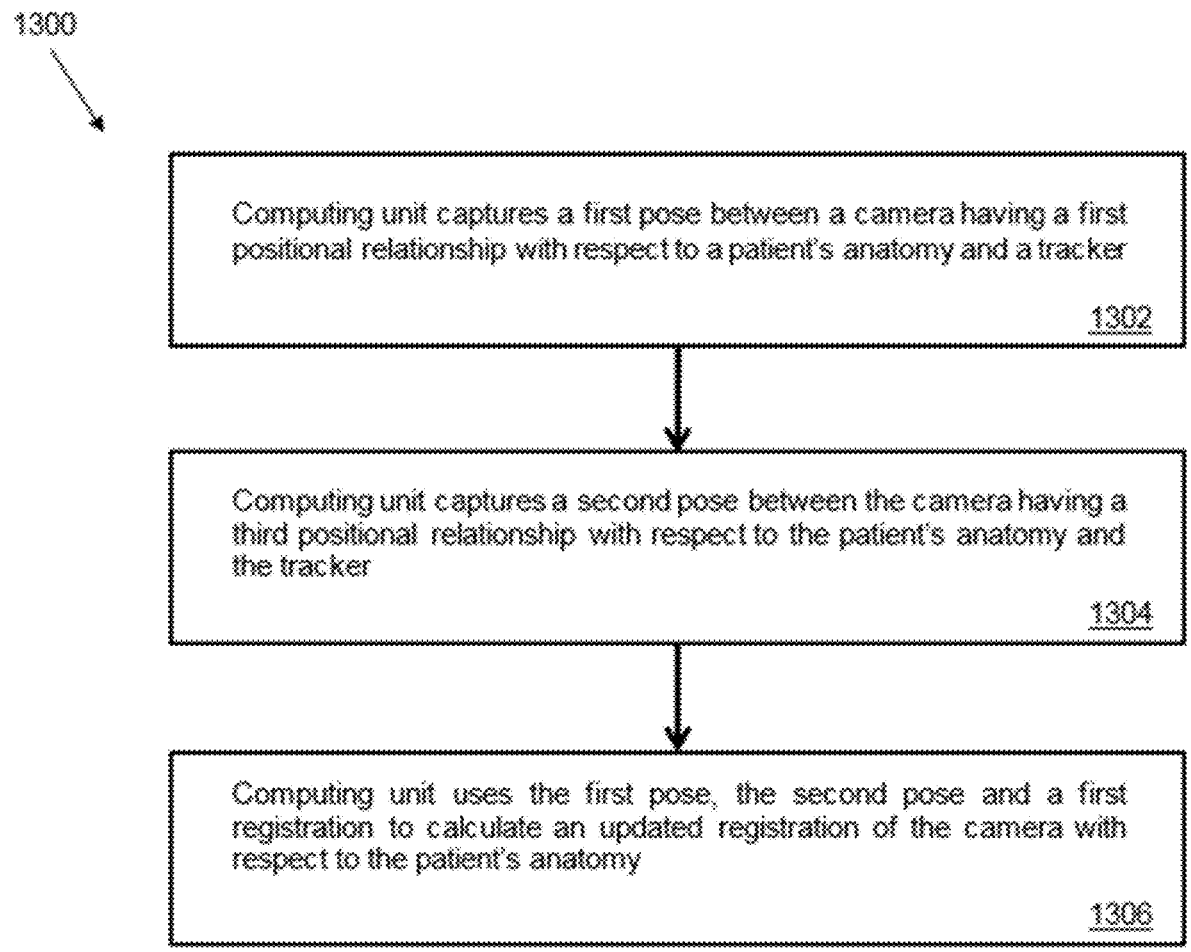
FIG. 13 depicts a computer implemented method for updating a registration of a camera with respect to a patient's anatomy when the camera is moved from a first pose to a second pose, based on the camera's pose relative to a tracker and the patient's anatomy.

Reference is now made to FIG. 13 depicting a computer-implemented method 1300 for updating a registration of a camera 102 with respect to a patient's anatomy 112 when the camera 102 is moved from a first pose to a second pose, based on the camera's pose relative to a tracker 708 and the patient's anatomy 112. A computing unit 114 captures (at 1302) a first pose between the camera 102 having a first positional relationship with respect to the patient's anatomy 112 and the tracker 708. The computing unit 114 captures (at 1304) a second pose between the camera 102 having a third positional relationship with respect to the patient's anatomy 112 and the tracker 708. Using the first pose, the second pose and a first registration, the computing unit 112 calculates (at 1306) an updated registration of the camera 102 with respect to the patient's anatomy 112.

Visualization of Patient's Anatomy

During the planning and execution of an image-guided medical intervention, visualization of the patient's anatomy 112 relative to the navigation system is required. A "4-up" style visualization of the patient's anatomy may be used to display a multiple planes of a three dimensional ("3D") medical image (e.g. MRI or CT image) of the patient's anatomy 112.

Figure 14:
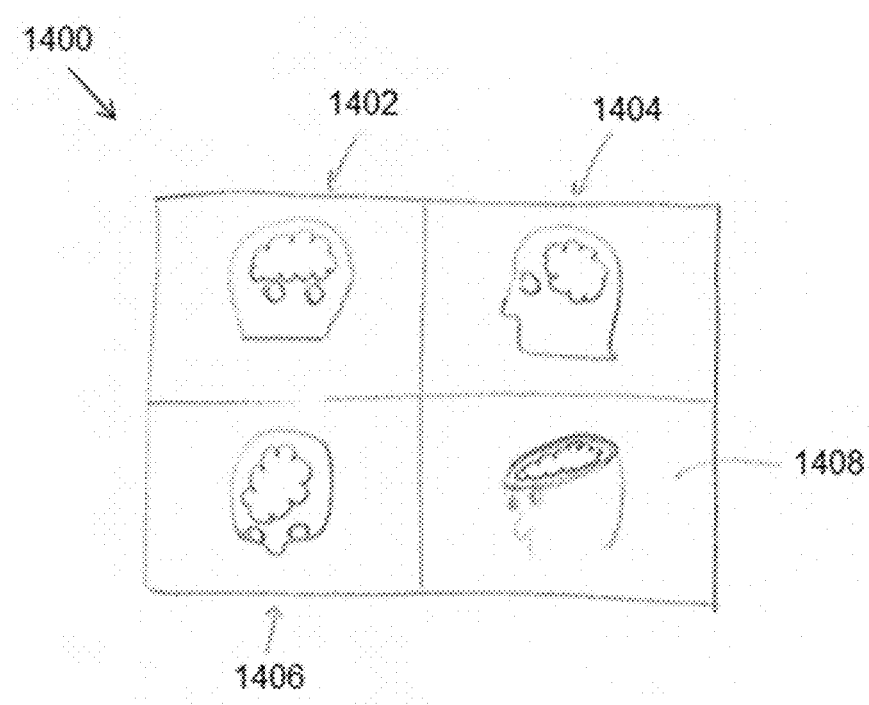
FIG. 14 depicts a 4-up view of the visualization medical images of a patient's anatomy.

FIG. 14 illustrates a "4-up" view 1400 that would be displayed on a display of a computing unit in an intra-operative localization system. The "4-up" style of visualization 1400 includes, for a current location within the patient's 3D medical image: (1) a two dimensional cross-section of the 3D medical image in the coronal plane 1402 of the patient's anatomy 112, (2) a two dimensional cross-section of the 3D medical image in the sagittal plane 1404 of the patient's anatomy 112, (3) a two dimensional cross-section of the 3D medical image in the transverse plane 1406 of the patient's anatomy 112, and (4) and isometric view 1408 of the 3D medical image.

During navigation in a surgical procedure, the "4-up" view 1400 may update in real-time based on the position of a navigated surgical instrument 110. For example, the two-dimensional coronal, sagittal and transverse cross-sections of the 3D medical image (1402, 1404, 1406) may be updated in real time to reflect the position of the a tracked probe, where the plane of the coronal, sagittal and transverse two dimensional cross-sections of the 3D image (1402, 1404, 1406) reflect the current tip of the probe relative to the patient's anatomy 112.

The isometric view 1408 may be modified to enhance visualization of the anatomical features of interest. For example, the isometric view 1408 may be modified to provide cut-away views of the patient's anatomy 112 such that regions of interest inside the anatomical volume, for example the brain, may be displayed. The regions of interest may include structures or lesions identified during pre-operative planning. Further, the regions of interest may be displayed in a way that is visibly distinguished from other areas within the anatomy. For example, the areas of interest may be pre-operatively identified and may be pre-operatively segmented within the medical image such that they may be viewed and/or manipulated independently from the other anatomy.

Figure 15:
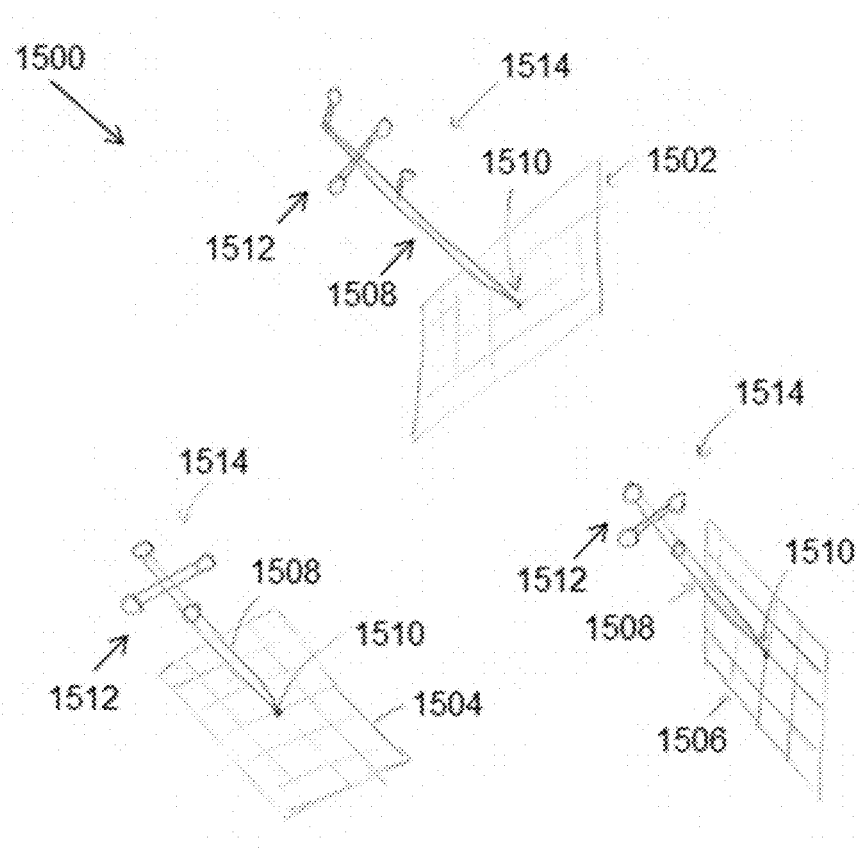
FIG. 15 depicts orthogonal cut-planes defined relative to a probe.

The isometric view 1408 may be modified in real-time based on the pose of a tracked probe. For example, the cut-away view of the patient's anatomy 112 may be displayed based on the pose of the tracked probe. FIG. 15 illustrates orthogonal three-dimensional cut-planes 1500 defined by the pose of a probe 1514. The probe may comprise a shaft 1508, a tip 1510, and a body 1512 with optically trackable features. A first cut-plane 1502 is defined as being perpendicular to the shaft 1508 of the probe 1514 and containing the point defined by the tip 1510 of the probe 1514. A second cut-plane 1504 is defined as being parallel to the front face of the probe 1514 and containing the vector defined by the shaft 1508 of the probe 1514. A third cut-plane 1506 is defined as being perpendicular to the front face of the probe 1514 and containing the vector defined by the shaft 1508 of the probe 1514.

Figure 16:
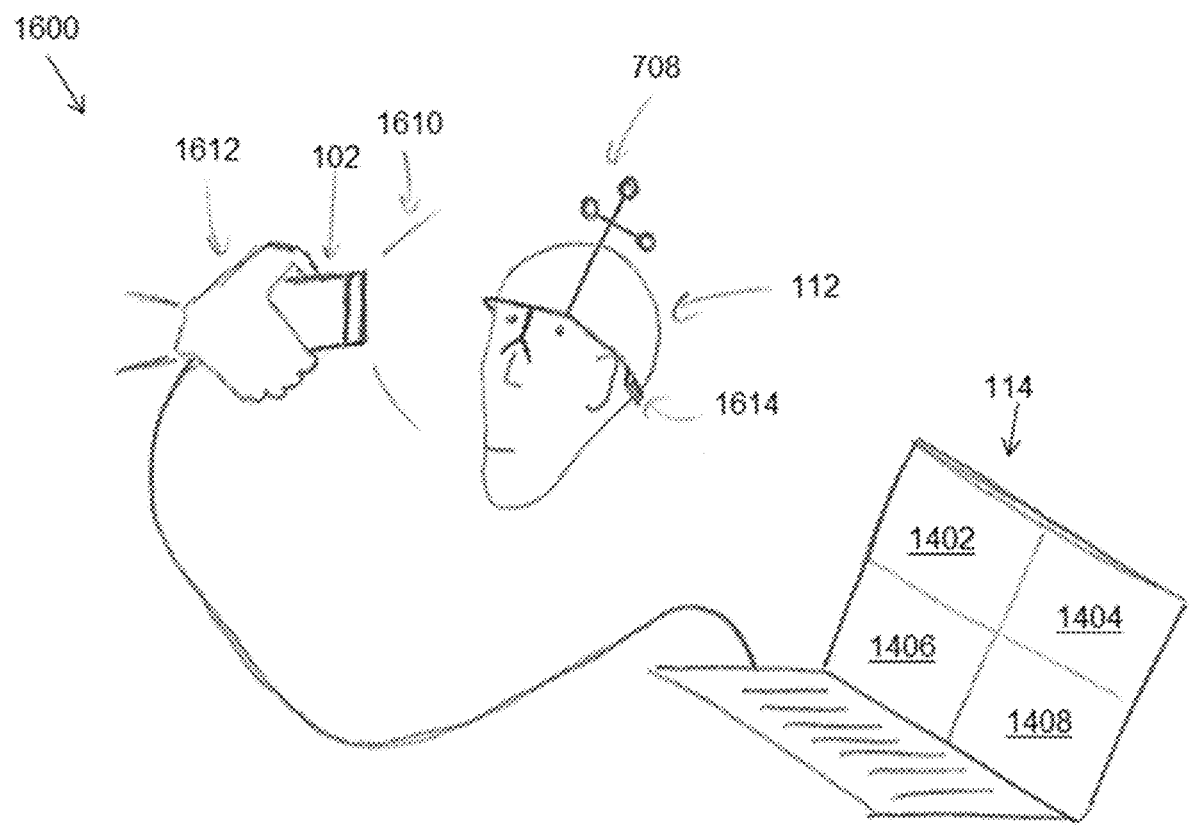
FIG. 16 depicts a handheld intra-operative localization system wherein a camera is moveable in a user's hand and a tracker is mounted to a structure on the patient's head.

FIG. 16 illustrates a hand-held intra-operative localization system 1600 showing camera 102 held in a user's hand 1612, while tracking the pose of a tracker 106 in the field of view 1610 of the camera 102 where the tracker 708 is registered to the patient's anatomy 112 (i.e. head). The registration includes image registration of a patient medical image to the patient anatomy 112. The tracker 708 is fixedly attached to the patient's anatomy 112 which may be accomplished, for 1614 may be attached to a head-clamp 104, or the mounting structure 1614 may be affixed directly to the patient's anatomy 112 (e.g. via bone screws, suction cups, elastic straps, or structures, such as a glasses-style frame for referencing off of a patient's features such as ears, nose, eyes), or a tracker 708 may comprise individual fiducial markers attached to the patient's anatomy 112 forming a trackable array. In some applications, it may be advantageous for the tracker 708 to be attached with non-invasive means (e.g. suction cups, elastic straps, glasses frames, stickers, individually attachable fiducial markers, clamps). In some applications, it may be advantageous for the tracker 708 to be rigidly anchored directly to bone using invasive means, such as bone screws. In the exemplary embodiment depicted in FIG. 16, a tracker 708 is attached to a patient's anatomy 112 (i.e. head) via a mounting structure 1614 that includes a head band and a frame that contacts a patient's ears and the bridge of their nose. In this embodiment, the pose of the camera 102 may be used to modify the visualization displayed on the computing unit 114, for example, by modifying any of the coronal, sagittal and transverse two dimensional cross-sections 1402, 1404, 1406 and the isometric view 1408 to correspond to the camera 102 coordinate-frame.

Figure 17:
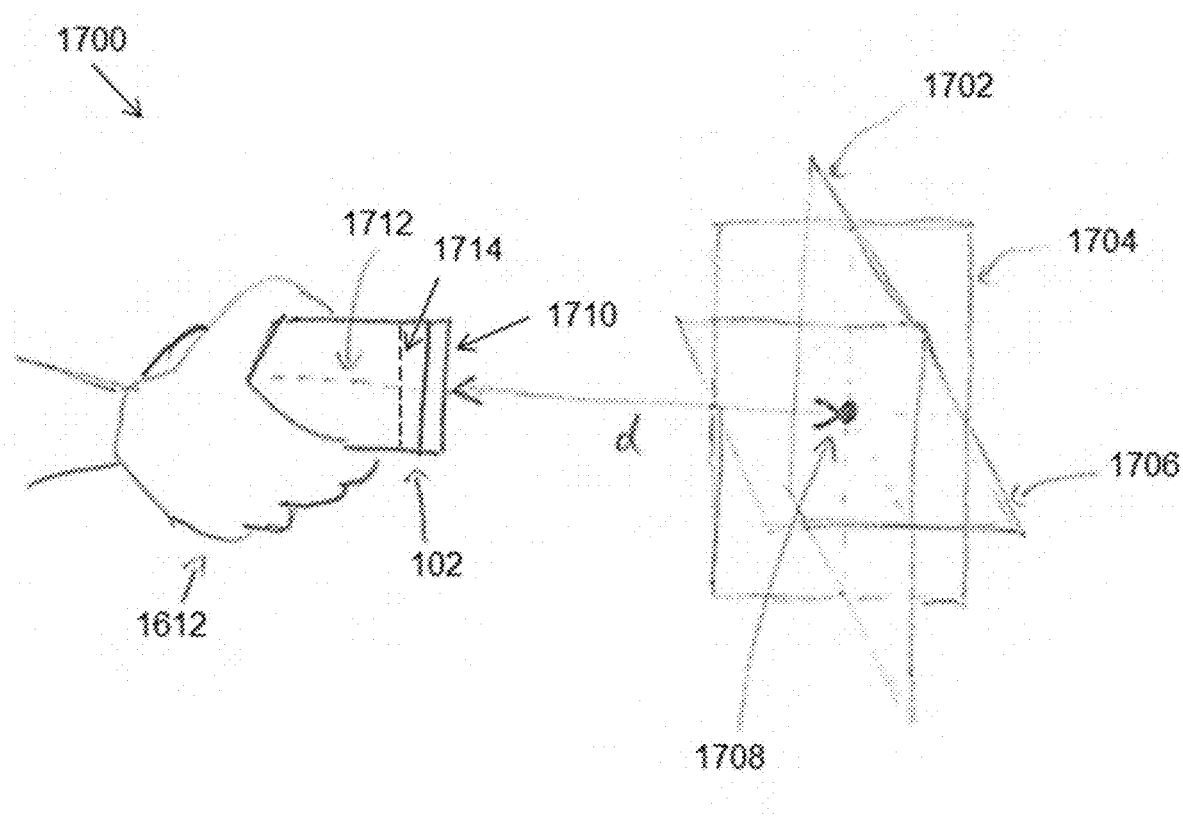
FIG. 17 depicts orthogonal reference planes defined by the pose of the camera coordinate frame.

FIG. 17 illustrates orthogonal camera-based reference planes 1700 defined by the camera coordinate-frame. The camera 102 may be held in a user's hand 1612 and the orthogonal three-dimensional cut-planes 1700 will be defined to correspond with the current pose of the camera 102. The camera-based reference plane used to modify the coronal plane 1402 displayed in the 4-up view 1400 is referred to as the coronal' plane 1702. The camera reference plane used to modify the sagittal plane 1404 displayed in the 4-up view 1400 is referred to as the sagittal' plane 1704. The camera reference plane used to modify the transverse plane 1406 displayed in the 4-up view 1400 is referred to as the transverse' plane 1706. Each of the orthogonal reference-planes (the coronal' plane 1702, the sagittal' plane 1704, and the transverse' plane 1706) may share a common origin 1708 displaced from the camera 102. In the exemplary embodiment depicted in FIG. 17, the origin 1708 is displaced by a distance "d" from the camera 102 along the optical axis 1712. The distance "d" may be any distance and may be selected by the user. Further, the distance "d" may be selected such that when any anatomy of interest is located at the origin 1708, the tracker 708 is viewable by the camera 102 (i.e. the tracker 708 is within the camera's working volume). The coronal' plane 1702 may be further defined as being parallel to the plane of the camera's optical imager 1710 and perpendicular to the optical axis 1712 of the camera 102. The sagittal' plane 1704 may be further defined as being perpendicular to the plane of the camera's optical imager 1710 and parallel to the vector of the vertical axis 1714 of the camera 102. The transverse' plane 1706 may be further defined as being perpendicular to the plane of the camera's optical imager 1710 and perpendicular to the vector of the vertical axis 1714 of the camera 102. The coronal' plane 1702, sagittal' plane 1704 and transverse' plane 1706 may be used instead of anatomical planes to visualize the patient's anatomy 112 via the slices depicted in the 4-up style visualization displayed on the display of the computing unit 114. Alternatively, the patient's anatomical reference planes may be used. The system may allow a user to select which reference planes (i.e. camera-based or patient based) are displayed, for example, via buttons located on the camera 102. The isometric view 1408 may also be modified to correspond to the camera-based reference planes 1702, 1704, 1706, either in conjunction with, or independently from, the two-dimensional slices. In the event the isometric view 1408 is modified independently from the slices to correspond to the camera-based reference planes 1702, 1704, 1706, the two-dimensional slices in the 4-up style visualization displayed on the display of the computing unit 114 will remain based on the coronal, sagittal and transverse patient reference planes.

Figure 18:
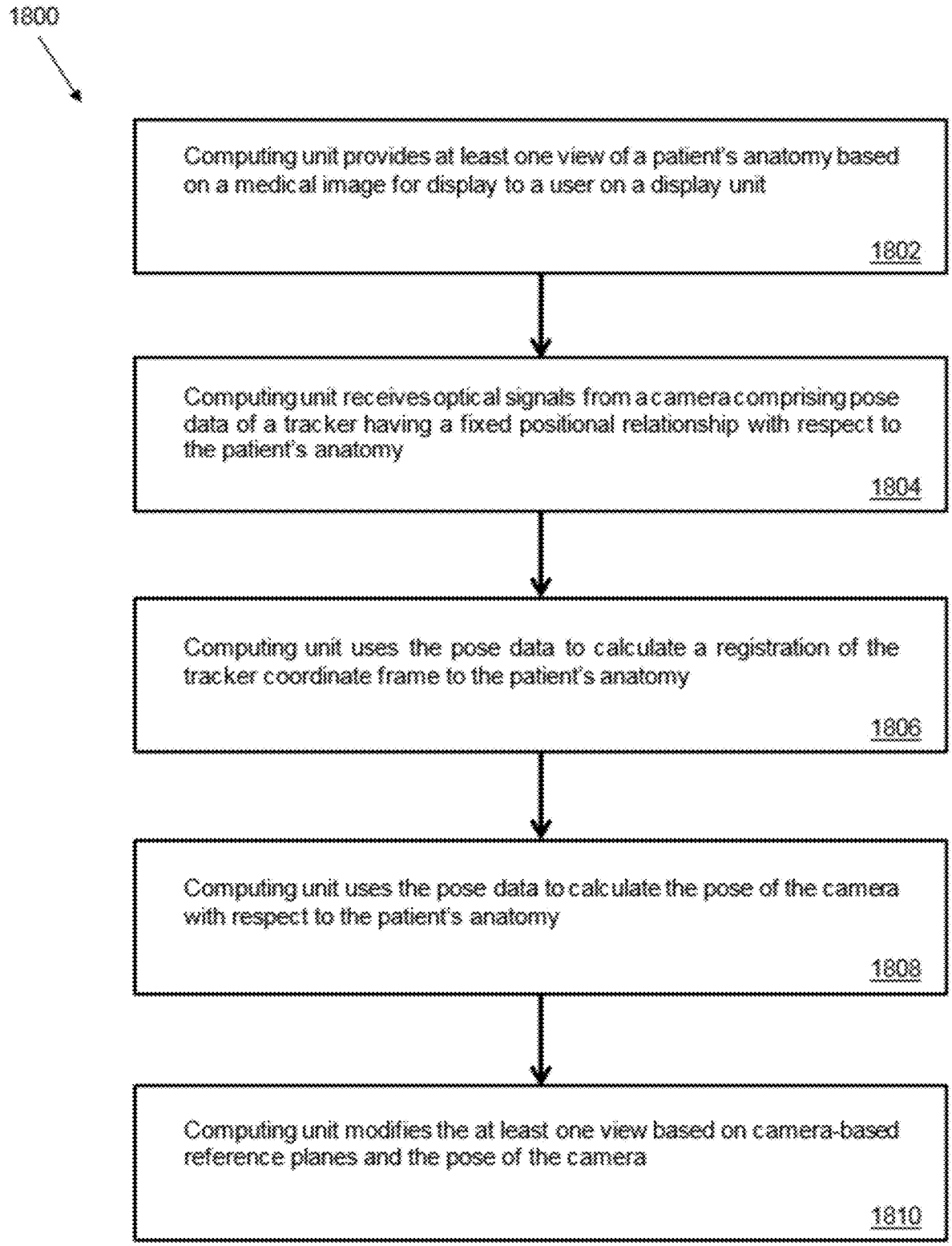
FIG. 18 depicts a computer implemented method for modifying a view of a patient's anatomy in a medical image based on camera reference planes and the pose of a camera.

Reference is now made to FIG. 18 depicting a computer-implemented method 1800 for modifying a view of a patient's anatomy in a medical image based on camera reference planes and the pose of a camera. A computing unit 114 provides (at 1802) at least one view of the patient's anatomy 112 for display to a user on a display unit. The computing unit 114 receives (at 1804) optical signals from a camera 102 comprising pose data of a tracker 708 having a fixed positional relationship with respect to the patient's anatomy 112. Using the pose data, the computing unit 114 calculates (at 1806) a registration of the tracker coordinate frame to the patient's anatomy 112 and (at 1808) the pose of the camera 102 with respect to the patient's anatomy 112. The computing unit modifies (at 1810) the at least one view based on camera-based reference planes and the pose of the camera 102 with respect to the patient's anatomy 112.

To aid in improving the visual relationship between the views displayed on the display of the computing unit 114 and the camera 102, where the views displayed on the display of a computing unit 114 are based on or modified by the camera-based reference planes 1702, 1704, 1706, the camera 102 may provide a projector for projecting a visible pattern onto the patient's anatomy 112. The projector may be any means of projecting the visible on the patient anatomy 112. For example, the visible pattern may be generated via two planar lasers, the planar lasers being perpendicular to each other, and parallel to the sagittal' plane 1704 and transverse' plane 1706, and further passing through the origin 1708, displaced from the camera by distance "d". In this way, the location of where the reference planes intersect with the patient's outer surface (e.g. their skin) may be physically represented on the patient, while the views displayed on the display of the computing unit 114 are based on those same reference planes. Alternatively, a line projecting laser may be used, the line passing through the origin. Therefore, a user may have an enhanced ability to visualize a patient's anatomy 112 based on the displayed views and the projected pattern on the patient.

Figure 19:
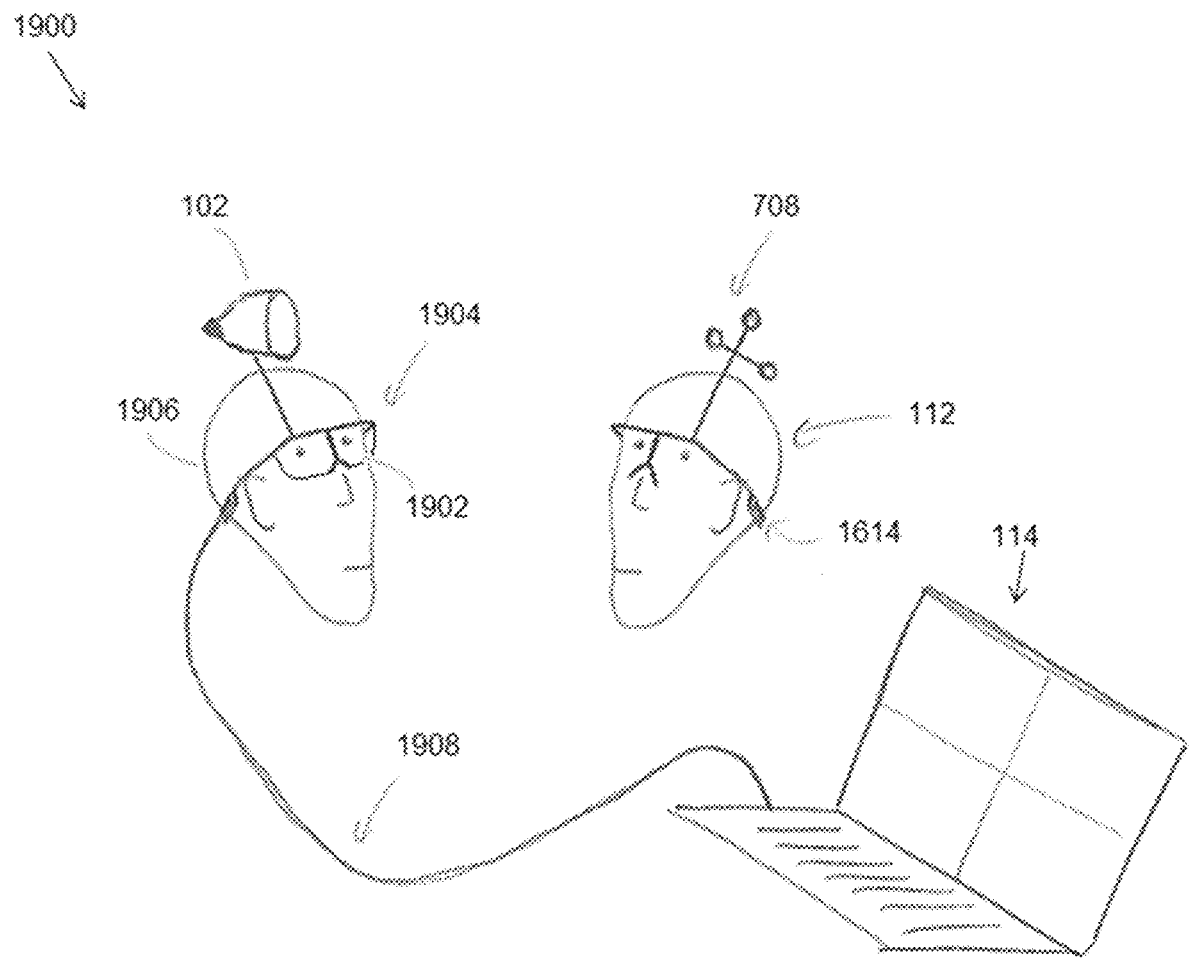
FIG. 19 depicts a head-mounted intra-operative localization system wherein a camera is mounted to a structure of a user's head and a tracker is mounted to a structure on the patient's head.

With reference to FIG. 19, in another embodiment, rather than being handheld, the camera 102 and a display 1902 may be head-mounted and may be contained in an augmented reality headset 1904 worn by the surgeon 1906. Display 1902 may include a projector and a surface upon which to project. In the illustration of FIG. 19, the surface may be a glass or plastic surface of the headset, such as a lens carried by an eyeglasses frame. The headset 1904 may be coupled to computing unit 114 such as via one or more cables/cabling 1908 providing an augmented reality system 1900. Computing unit 114 may also comprise an integrated display device (e.g. display screen) for presenting information to the surgeon or others. As described herein, the computing unit 114 can compute the pose of the camera 102 relative to the tracker 708 and patient anatomy 112 as the surgeon 1906 moves their head, thus ensuring the proper alignment of the overlay of the virtual view of the patient anatomy 112 on the user's actual view of the patient. The headset may incorporate computing unit 114 itself (not shown). The camera may be located closer to an eye of the surgeon, such as on a corner of the frame of the headset, in front of a portion of the glass/plastic lens to more closely align with the surgeon's field of vision.

The augmented reality display in such an augmented reality system is preferably transparent to allow the surgeon to see through the display of the computing unit 114 to directly see the patient. The computing unit 114 may receive a real-time feed from the camera 112 of the patient anatomy. This real-time feed from the camera 112 may be displayed on the augmented reality display of the computing unit 114. The overlaid virtual view of the patient's anatomy 112 may be opaque or partially transparent. In any headset embodiment, it may be preferable to only display a single view, rather than the "4-up" view displayed on a non-augmented reality display of a computing unit 114. If a single view is presented, it may be based on the coronal' plane 1702 and the origin 1708. A virtual view of any pre-identified regions of interest (pre-identified in the patient's medical image) may also be persistently displayed from a perspective that matches camera's 102 coordinate-frame and thus be representative of the user's actual perspective of the patient's anatomy 112.

The advantage of these alternative embodiments that modify the 4-up view based on the pose of the camera, whether hand-held or head-mounted, is that it displays the underlying patient anatomy 112 in a more intuitive manner to the user.

Further, the relative pose between the tracker 708, which is attached to the patient, and the camera 102, whose pose can be manipulated by a user, may be used to control the pan and tilt of an isometric view 1408, displayed to the user. The camera 102 may provide a button, which when pressed, causes the computing unit 114, connected to the camera 102, to enter a pan or tilt mode, in which the changes to the relative pose of the tracker 708 and camera 102 cause a change to the pan and/or tilt of the displayed isometric view 1408. In tilt mode, for example, a change in the relative pose of the tracker 708 and camera 102 results in a corresponding change in the tilt of the displayed isometric view 1408 of the medical image. In pan mode, for example, a relative translation of the tracker 708 and camera 102 causes a corresponding translation of the isometric view 1408 of the medical image.

Planning Navigational Procedures

Figure 20:
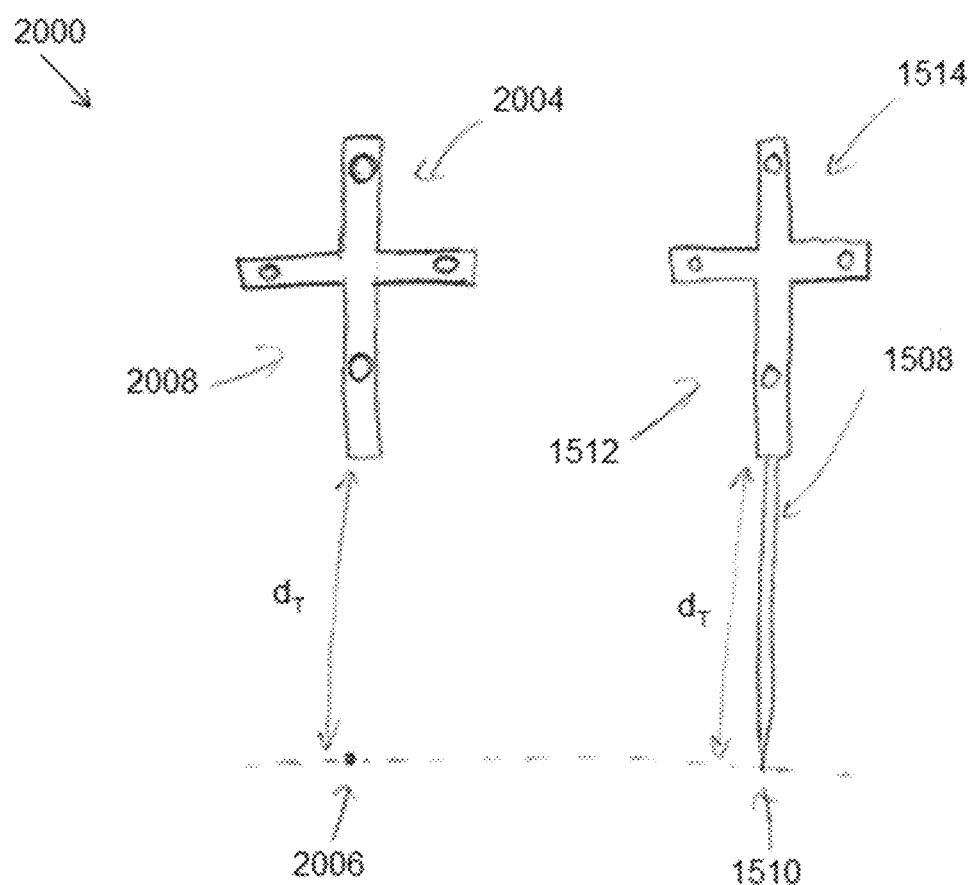
FIG. 20 depicts a probe and corresponding virtual probe.

In an embodiment, with reference to FIG. 20, an intra-operative localization system may provide a virtual probe to aid in planning the navigation of the surgical procedure. FIG. 20 illustrates a corresponding probe and virtual probe pair 2000. The system provides a virtual probe 2004 comprising a body 2008, the body 2008 with optically trackable features and a location for a user to grasp or a handle, the virtual probe 2004 may not have a physical shaft or tip. An intra-operative localization system using a virtual probe 2004 may further comprise a computing unit 114 that has access to the location of the virtual tip 2006 of the virtual probe 2004 which is located a distance, "$d_T$", from relative to the body 2008. For example, computing unit stores or has access to a stored definition of the virtual probe (e.g. a probe model). The computing unit 114 then provides a navigational display of the patient's anatomy 112, where the displayed view(s) are modified based on the position of the virtual tip 2006 of the virtual probe 2004. The system may also provide a probe 1514, comprising a body 1512 with optically trackable features and a location for a user to grasp, as well as a shaft 1508 and a tip 1510 extending from the body 1512. The probe 1514 and the virtual probe 2004 may have similar or identical features on the respective bodies 1512, 2008. The main difference between the two probes 1514, 2004 may be that the probe 1514 provides a physical shaft 1508 with a tip 1510 for localization, whereas the virtual probe 2004 does not. In a further embodiment, the virtual tip 2006 location relative to the virtual probe body 2008 (as accessed by the computing unit 114) is the same as the physical tip 1510 location of the probe 1514 relative to the probe body 1512. The system may further be configured to provide the virtual probe 2004 for non-sterile use, and the probe 1514 for sterile use.

There is disclosed a system for performing a navigated medical procedure, the system comprising: A camera configured to be mounted relative to a patient's anatomy by a mounting arm, the camera being configured to detect optical signals comprising pose information of an object at the surgical site, and providing the optical signals to a computing unit for calculating pose; a tracker configured to provide optical signals for detection by the camera, the tracker attached to or inherently a part of the object; the mounting arm further configured to provide positional adjustment to orient the camera toward the surgical site; the camera and mounting arm being further configured to be enclosed within a sterile camera drape for use within a sterile field; the position of the camera relative to the anatomy not changing when enclosed within the sterile camera drape.

The system may further include the sterile camera drape. The sterile camera drape may further provide a window to allow for optical transmission of signals comprising pose information. The system may further comprise a shroud for securing the sterile camera drape to the camera. The camera may further comprise shroud features to mate the shroud with the camera to secure the sterile camera drape. The system may be configured to secure the sterile camera drape to the camera such that the window is secured in alignment with the optical path of the camera. The shroud may be configured to secure the camera drape to the camera via spring forces.

The mounting arm may be configured to rigidly attach to the camera. The system may further comprise a camera clamp to rigidly hold the camera, the camera clamp being further configured to provide a mounting mechanism to the mounting arm. The mounting arm may be configured to releasably and repeatably attach to the camera. The camera or camera clamp may provide a kinematic mounting mechanism and the mounting arm may provide a complementary kinematic mounting mechanism. The mounting arm may be configured to provide positional alignment via lockable joints.

The mounting arm may comprise at least one joint for positional adjustment where the at least one joint is a lockable ball joint. The mounting arm may comprise multiple joints where the multiple joints are lockable by a single user-adjustable mechanism. The mounting arm positional adjustment may be performed when enclosed within the sterile camera drape, for example via adjustment members that are gripable through the drape.

The mounting arm may be configured for mounting to a patient immobilizer or a patient positioner. The patient immobilizer may be a head clamp.

The mounting arm may configured for rigid fixation to the patient's anatomy. Rigid fixation may be provided through a Mayfield clamp or secured to the patient's anatomy via bone screws.

The patient's anatomy may be one of a cranium, a spine, a pelvis, a femur, a tibia, a hip, a knee, a shoulder, an ankle.

There is disclosed a system for performing a navigated surgical procedure, the system comprising: a sterile camera drape configured to provide a sterile barrier for a camera mounting arm and a camera attached thereto. The sterile drape may be configured to allow positional adjustment of the positionally-adjustable camera mounting arm when providing the sterile barrier.

The sterile camera drape may further provide a window to allow for optical transmission of signals comprising pose information from the camera to a computing unit. The sterile camera drape window may be made of a rigid, thin and flat optically transparent material. The sterile camera drape may be configured to be secured in alignment with a camera such that the optical window is in alignment with the optical path of the camera.

The sterile camera drape may be configured to extend from the camera to at least the base of the camera mounting arm.

The sterile camera drape may comprise a mechanism for providing a continuous sterile barrier with a patient drape. The mechanism may be a sterile elastic band, configured to tightly hold together the patient drape with the sterile camera drape. The mechanism may be an adhesive strip, which is configured to be applied at a location where the sterile camera drape and patient drape intersect. The mechanism may be a plurality of adhesive sections encircling the sterile camera drape at various locations along the length of the sterile camera drape, configured to enable circumferential adhesion to a patient drape at a desired location along the length of the camera drape.

There is disclosed a system for performing a navigated medical procedure, the system comprising: a mounting arm, configured to attach to a camera configured to detect optical signals comprising pose information of objects at a surgical site and providing the optical signals to a computing unit for calculating pose, the mounting arm having proximal end comprising an attachment mechanism, and a distal end comprising a base mounting mechanism.

The mounting arm may comprise a user-adjustable mechanism to adjust the relative position and orientation of the proximal and distal ends in up to 6 DOF. The user-adjustable mechanism may comprise at least one lockable ball joint. The user-adjustable mechanism may comprise a gooseneck mechanism.

The base mounting mechanism may be configured to attach to one of: a mobile cart, an operating table, providing a compatible clamp for operating room table rails, a head clamp, providing a starburst connector.

The mounting arm may comprise a second connector at the distal end. The second connector may comprise a same connector that is complementary to the base mounting mechanism.

The mounting arm may be further configured to selectively attach to a tracker.

The system may comprise a second mounting arm, the second mounting arm configured to attach to a tracker. The second mounting arm may be configured to attach to a sterile tracker and a non-sterile tracker, for example, one at a time. The second mounting arm may be configured to attach to a sterile tracker through a sterile patient drape.

There is disclosed a system for performing a navigated medical procedure, the system comprising: a virtual probe comprising a body providing a tracker and a surface (e.g. handle) to be grasped by a user, the tracker of the virtual probe configured to provide optical signals comprising pose data to a camera in communication to a computing unit, the computing unit configured to provide a view of a patient's anatomy for display, the view of the patient's anatomy being based on a medical image, the computing unit further configured to modify the view based on a registration and further based on a location of a tip of the virtual probe, the location of the tip of the virtual probe relative to the pose of the tracker represented by the pose data being accessible in a memory to the computing unit.

The view may be modified to show the location of the tip of the virtual probe in the medical image. The medical image may be one of a CT-scan and an MRI-scan.

The system may further comprise a probe comprising a body comprising a tracker and a user-graspable aspect, and further comprising a shaft and a tip extending from the body.

The location of the tip of the virtual probe may have the same positional relationship to the virtual probe tip body as the positional relationship between the probe tip and the probe body.

The virtual probe may be provided for non-sterile use and the probe being provided for sterile use.

The patient's anatomy may be a cranium and brain. The patient's anatomy may be a hip or knee. The patient's anatomy may be a vertebrae.

It is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

Various embodiments have been described herein with reference to the accompanying drawings. It will, however, be evident that various modifications and changes may be made thereto, and additional embodiments may be implemented, without departing from the broader scope of the disclosed embodiments as set forth in the claims that follow.

The invention claimed is:

1. A method comprising:
providing a non-sterile camera releasably coupled to a distal end of a non-sterile camera mounting arm and a proximal end of the non-sterile camera mounting arm releasably coupled to a surgical clamp immobilizing a patient's anatomy to perform a registration;
using a computing unit of a surgical navigation system to perform the registration between a coordinate frame of the non-sterile camera and the patient's anatomy from pose data communicated to the computing unit from the non-sterile camera;
following the registration, draping the non-sterile camera and the non-sterile camera mounting arm by a camera drape to provide a sterile barrier between the patient's anatomy and the non-sterile camera and non-sterile camera mounting arm, where the draping is performed without moving a position of the camera relative to the patient's anatomy, following the draping, using the computing unit to calculate poses of sterile instruments relative to the patient's anatomy using the registration to provide surgical navigation during a surgical procedure, the poses of the sterile instruments calculated using pose data received from the non-sterile camera as draped, along with the non-sterile camera mounting arm, in the camera drape to provide a sterile barrier between the patient's anatomy and the non-sterile camera and non-sterile camera mounting arm, the camera remaining in a same position relative to the patient's anatomy to provide the pose data for the sterile instruments as used to provide the pose data for the registration.

2. The method of claim 1, wherein the pose data received from the non-sterile camera as draped is defined from optical signals transmitted to the non-sterile camera through the camera drape without distortion.

3. The method of claim 1 comprising using non-sterile instruments to provide the pose data for performing the registration.

4. The method of claim 1, wherein the camera drape comprises a drape optical window, wherein the draping comprises applying a holding mechanism to hold the drape optical window in a fixed and correct alignment with optics of the non-sterile camera.

5. The method of claim 1 comprising:
prior to the registration, rigidly fixing a non-sterile tracker relative to the patient's anatomy and wherein the pose data communicated to the computing unit from the non-sterile camera to perform the registration comprises pose data of the non-sterile tracker rigidly fixed relative to the patient's anatomy to perform the registration; and
replacing the non-sterile tracker with a sterile tracker rigidly fixed relative to the patient's anatomy and wherein the poses of the sterile instruments are calculated to provide the surgical navigation without performing a second registration.

6. The method of claim 5 comprising using a same tracker mounting arm to rigidly fix the non-sterile tracker and, later, the sterile tracker in the same position.

7. The method of claim 6, wherein the using of the computing unit to calculate the poses of sterile instruments comprises using the computing unit to factor in a difference between a geometry of the non-sterile tracker and a geometry of the sterile tracker.

8. The method of claim 1, wherein the patient's anatomy is a cranium.

9. A method comprising:
providing a non-sterile tracker and a sterile tracker, the non-sterile tracker for use during a non-sterile stage of a surgery for a patient and the sterile tracker for use in place of the non-sterile tracker during a sterile stage of the surgery for the patient;
using a computing unit of a surgical navigation system to store differences between geometries of the non-sterile tracker and the sterile tracker;
using the computing unit to calculate a registration of a camera with respect to the non-sterile tracker during the non-sterile stage;
during the sterile stage where the sterile tracker is used in place of the non-sterile tracker and the patient is draped with a patient drape, using the computing unit to perform surgical navigation responsive to the registration and the differences stored by the computing unit to calculate poses.

10. The method of claim 9, wherein:
the patient drape comprises a sterile tracker adaptor;
the method includes using the computing unit to store a relative position between i) the non-sterile tracker when mounted to a mounting arm before the patient drape is applied and ii) the sterile tracker when mounted to the mounting arm via a sterile tracker adaptor after the patient drape is applied, wherein the relative position is based on geometrical properties of the sterile tracker adaptor; and
the using of the computing unit to perform surgical navigation is responsive to the relative position stored by the computing unit to calculate the poses.

11. A system comprising:
a non-sterile camera, a non-sterile camera mounting arm, and a camera drape, the non-sterile camera configured to releasably couple to a distal end of the non-sterile camera mounting arm and a proximal end of the non-sterile camera mounting arm configured to releasably couple to a patient's anatomy, as immobilized, to perform a registration; and
a computing unit comprising a processor and a storage unit coupled thereto, the storage unit storing instructions, which, when executed by the processor, cause the computing unit to:
perform the registration between a coordinate frame of the non-sterile camera and the patient's anatomy, wherein the non-sterile camera is releasably coupled to the distal end and the proximal end is releasably coupled to the patient's anatomy, as immobilized, and the computing unit uses pose data communicated from the non-sterile camera to perform the registration; and,
calculate poses of sterile instruments relative to the patient's anatomy using the registration to provide surgical navigation during a surgical procedure, the poses calculated following a draping of the non-sterile camera and the non-sterile camera mounting arm by the camera drape to provide a sterile barrier between the patient's anatomy and the non-sterile camera and non-sterile camera mounting arm, where the draping is performed without moving a position of the camera relative to the patient's anatomy.

12. The system of claim 11, wherein the camera drape is configured to permit a transmission of optical signals to the non-sterile camera through the camera drape without distortion.

13. The system of claim 12, wherein the camera drape comprises a camera window and wherein the system comprises a camera shroud configured to hold the camera drape in place on the camera to receive optical signals through the camera window without distortion.

14. The system of claim 11, wherein the registration is performed using pose data of non-sterile instruments.

15. The system of claim 11, wherein the instructions cause the computing unit to:
receive, from the non-sterile camera, pose data of a non-sterile tracker rigidly fixed relative to the patient's anatomy to perform the registration; and
following the draping, receive, from the non-sterile camera as draped, pose data of a sterile tracker rigidly fixed relative to the patient's anatomy to provide the surgical navigation without performing a second registration.

16. The system of claim 15, wherein:
the system further comprises a tracker mounting arm;
the pose data of the non-sterile tracker comprises pose data of the non-sterile tracker rigidly fixed via the tracker mounting arm to position the non-sterile tracker in a tracker position for performing the registration; and the pose data for calculating the poses of the sterile instruments comprises pose data of the sterile tracker affixed to the tracker mounting arm to position the sterile tracker in the tracker position to calculate the poses of the sterile instruments.

17. The system of claim 16, wherein the poses of the sterile instruments as calculated are responsive to a geometry of the non-sterile tracker differing from and a geometry of the sterile tracker.

18. The system of claim 11, wherein the patient's anatomy is a cranium.

19. A system comprising:
a non-sterile camera, a non-sterile camera mounting arm, and a camera drape, the non-sterile camera configured to releasably couple to a distal end of the non-sterile camera mounting arm and a proximal end of the non-sterile camera mounting arm configured to releasably couple to a patient's anatomy, as immobilized, to perform a registration; and a computing unit comprising a processor and a storage unit coupled thereto, the storage unit storing instructions, which, when executed by the processor, cause the computing unit to:
store differences between geometries of a non-sterile tracker and a sterile tracker, the non-sterile tracker for use during a non-sterile stage of a surgery for a patient and the sterile tracker for use in place of the non-sterile tracker during a sterile stage of the surgery for the patient;

calculate a registration of a camera with respect to the non-sterile tracker during the non-sterile stage; and use the registration and the differences stored to calculate poses during the sterile stage where the sterile tracker is used in place of the non-sterile tracker and the patient is draped with a patient drape.

20. The system of claim 19, wherein the patient drape comprises a sterile tracker adaptor, and the instructions cause the computing unit to:
before using the registration and the differences stored, store a relative position between i) the non-sterile tracker mounted to a mounting arm before the patient drape is applied and ii) the sterile tracker when mounted to the mounting arm via the sterile tracker adaptor after the patient drape is applied, wherein the relative position is based on geometrical properties of the sterile tracker adaptor; and during the sterile stage where the sterile tracker is used in place of the non-sterile tracker and the patient is draped with the patient drape, use the relative position stored to calculate the poses during the sterile stage.

* * * * *